(12) United States Patent
Chen et al.

(10) Patent No.: US 7,220,585 B2
(45) Date of Patent: May 22, 2007

(54) TRANSCRIPTION FACTOR STRESS-RELATED POLYPEPTIDES AND METHODS OF USE IN PLANTS

(75) Inventors: Ruoying Chen, Apex, NC (US); Nocha Van Thielen, Chapel Hill, NC (US); Oswaldo da Costa e Silva, Ludwigshafen (DE)

(73) Assignee: BASF Plant Science GmbH, Ludwigshafen (DE)

( * ) Notice: Subject to any disclaimer, the term of this patent is extended or adjusted under 35 U.S.C. 154(b) by 295 days.

(21) Appl. No.: 10/293,971

(22) Filed: Nov. 12, 2002

(65) Prior Publication Data
US 2003/0172408 A1 Sep. 11, 2003

Related U.S. Application Data

(60) Provisional application No. 60/344,503, filed on Nov. 9, 2001.

(51) Int. Cl.
*C12N 15/82* (2006.01)
*C12N 15/29* (2006.01)
*A01H 5/00* (2006.01)
*A01H 5/10* (2006.01)

(52) U.S. Cl. ............... 435/419; 800/298; 536/23.6; 435/320.1

(58) Field of Classification Search ............... 536/23.6; 435/320.1, 419; 800/298
See application file for complete search history.

(56) References Cited

U.S. PATENT DOCUMENTS 5,981,729 A   11/1999   Chun et al. ............... 536/23.6

FOREIGN PATENT DOCUMENTS

| WO | WO 98/09521 | 3/1998 |
| WO | WO 99/38977 | 8/1999 |
| WO | WO 00/53741 | 9/2000 |

OTHER PUBLICATIONS

Whisstock J.C. et al. Prediction of protein function from protein sequence and structure. Q Rev Biophys. Aug. 2003;36(3):307-40. Review.*
Liu Q. et al. Two transcription factors, DREB1 and DREB2, with an EREBP/AP2 DNA binding domain separate two cellular signal transduction pathways in drought- and low-temperature-responsive gene expression, . . . Plant Cell. Aug. 1998;10(8):1391-406.*
Doi A. et al. GenBank ACCESSION L29421, *Saccharomyces cerevisiae* DBF3 gene, complete cds, May 22, 1995.*
Quatrano R. et al. GenBank ACCESSION AW476911, ga38h10.y1 Moss EST library PPU *Physcomitrella patens* cDNA clone PEP_SOURCE_ID:PPU040820 5'similar to TR:O26807 O26807 Transcriptional Regulator. ;, mRNA sequence, Feb. 24, 2000.*
Babiychuk, Elena et al., "*Arabidopsis thaliana* NADPH Oxidoreductase Homologs Confer Tolerance of Yeasts toward the Thiol-oxidizing Drug Diamide", The Journal of Biological Chemistry, 270(44):26224-26231, 1995.
Bharti, Kapil et al., "Isolation and characterization of HsfA3, a new heat stress transcription factor of *Lycopersicon peruvianum*", The Plant Journal, 22(4):355-365, 2000.
Choisne, N. et al., "*Arabidopsis thaliana* chromosome 3, BAC clone T8P19", Accession No. AL133315, Dec. 2, 1999.
Jaglo-Ottosen et al., "*Arabidopsis* CBF1 Overexpression Induces COR Genes and Enhances Freezing Tolerance", Science, 280:104-106, 1998.
Kasuga et al., "Improving plant drought, salt, and freezing tolerance by gene transfer of a single stress-inducible transcription factor", Nature Biotech., 17:287-291, 1999.
Machuka, Jesse, et al., "Sequence analysis of Expressed Sequence Tags from an ABA-Treated cDNA Library Identifies Stress Response Genes in the Moss *Physcomitrella patens*", Plant Cell Physiol., 40(4), pp. 378-387, 1999.
Quatrano, R. et al., "ga02B09.y1 Moss EST library", Accession No. AW098572, Oct. 20, 1999.
Quatrano, R. et al., "ga31e07.y1 Moss EST library", Accession No. AW145337, Nov. 2, 1999.
Quatrano, R. et al., "gb19f04.y1 Moss EST library", Accession No. AW699069, Apr. 19, 2000.
Quatrano, R. et al., "*Physcomitrella patens* cDNA clone", Moss EST library, Accession No. AW477309, pp. 1-2, Mar. 2, 2000.
Quatrano, R. et al., "*Physcomitrella patens* cDNA clone", Moss EST library, Accession No. AW599790, pp. 1-2, Mar. 23, 2000.
Sakakibara, K. et al., "Homeobox Protein PPHB7", Accession No. Q9LS31, Oct. 1, 2000.
Sakakibara, K. et al., "*Physcomitrella patens* MRNA for homeobox protein PpHB7", Accession No. AB028078, Apr. 4, 2000.
Shinozaki et al., "Molecular responses to dehydration and low temperature: differences and cross-talk between two stress signaling pathways", Curr. Opin. Plant Biol., 3:217-223, 2000.
Winicov, I., "New Molecular Approaches to Improving Salt Tolerance in Crop Plants", Annals of Botany, 82:703-710, 1998.
Winicov, I. And Bastola, D.R., "Transgenic Overexpression of the Transcription Factor Alfin1 Enhances Expression of the Endogenous *MsPRP2* Gene in Alfalfa and Improves Salinity Tolerance of the Plants", Plant Physiology, 120:473-480, 1999.
Xiang, C. et al., "DNA-binding properties, genomic organization and expression pattern of *TGA6*, a new member of the *TGA* family of bZIP transcription factors in *Arabidopsis thaliana*", Plant Molecular Biology, 34:403-415, 1997.
Quatrano, et al., Database GenCore on EST, "Leeds/Wash U Moss EST Project," Accession No. BI894340, Oct. 15, 2001.

* cited by examiner

*Primary Examiner*—Cynthia Collins
(74) *Attorney, Agent, or Firm*—Elaine Sale; Mark Westhafer; Ruoying Chen

(57) ABSTRACT

A transgenic plant transformed by a Transcription Factor Stress-Related Protein (TFSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated TFSRPs, and isolated nucleic acid coding TFSRPs, and vectors and host cells containing the latter.

18 Claims, 1 Drawing Sheet pBPSJH001

SEQUENCE LISTING

<160> NUMBER OF SEQ ID NOS: 35

<210> SEQ ID NO 1
<211> LENGTH: 629
<212> TYPE: DNA
<213> ORGANISM: Physcomitrella patens

<400> SEQUENCE: 1

```
gcaccaggag gagccttaca tcagtgcagc cgagcttcga ttatatcctc actccggaag      60
ctcagatttc tccgcgccca tggggacaag tgaggaactt caggttgtgc acgagcaacg     120
atccgagtgt tgtagtggag ggcgcgttga acccttttgtt ctcaggtatg cgtgacgaca     180
atgaagcgat tactgcccat gctcgaatag ccggtaaccc tgtcgcgcct gacaccctgg     240
atggggttag atatccccag gaatacgaat acatttaaa  acacaagctg gagatggctt     300
gtgctgcagt cgccatgact cgggcaaagg caagacagac aagaggatca gcggaagcta     360
gtgttgggcg agcagaacca tccaccaaaaa tccaagcatc tggaacactt cctccgaaag     420
gaaaaacatc agcttgtaac cttcctgctg cggagaaatc cgatgcagat gtgggaaga      480
gtcgaccaat caccagcggc tcggaagtct ctgaagatga agaacatgac gagcagaacg     540
gaaagacagc acctggtgac atcaaacgcg tcaagaggat gctgtctaac cgcgaatctg     600
ccagaagatc tcgtaaagaa aacaggcca                                       629
```

<210> SEQ ID NO 2
<211> LENGTH: 1591
<212> TYPE: DNA
<213> ORGANISM: Physcomitrella patens

<400> SEQUENCE: 2

```
gcccttatcc cgggtcaagc tacgacgcct caatcttccc cccaatctcc cccccaagat      60
atgaacact  catcttccgt cgacgatctc gtgggcacat tctgggacga ttctgccgat     120
cttgtagaca aggcagcagc atccacgacg attaacagga gtgcatccga atggtctttt     180
caagaatttc ttaaagacag ccactccgct gccgctggcc caggggccct caagctgcgg     240
cctgcttgca agagccggtt cctgatggag catggcgatg tcaaggtgtg cgaacccgag     300
gcacagaaag tgaaggaatc tctcagggct gaggaggaag atgtaggtga ggagccttac     360
atcagtgcag ccgagcttcg attatatcct cactccggaa gctcagattt ctccgcgccc     420
atggggacaa gtgaggaact tcaggttgtg acgacaacg  atccgagtgt tgtagtggag     480
ggcgcgttga acccttttgtt ctcaggtatg cgtgacgaca atgaagcgat tactgcccat     540
gctcgaatag ccggtaaccc tgtcgcgcct gacaccctgg atggggttag atatccccag     600
gaatacgaat acatttaaa  acacaagctg gagatggctt gtgctgcagt cgccatgact     660
```

```
cgggcaaagg caagacagac aagaggatca gcggaagcta gtgttgggcg agcagaacca    720
tcaccaaaaa tccaagcatc tggaacactt cctccgaaag gaaaaacatc agcttgtaac    780
cttcctgctg cggagaaatc cgatgcagat gtgggaaaga gtcgaccaat caccagcggc    840
tcggaagtct ctgaagatga agaacatgac gagcagaacg gaaagacagc acctggtgac    900
atcaaacgcg tcaagaggat gctgtctaac cgcgaatctg ccagaagatc tcgtagaaga    960
aaacaggccc atttgagtga gctggaaatg caggtagctc aattgagggt tgagaataca   1020
aatctgttgc agagactcca agatatcagt caaaagttcc aagaagcagc tattgacaat   1080
cgtgttctca cggcagattg cgaagcctta cgtgccaagg tgaatatggc agcacgagat   1140
ttgatggcga ggcatggaca aattcctggt ggacaattta tcttggaacc cagcttgaga   1200
tatgtgttgc cttacgaaat gcagcccgtc gccgatgaat ccgcgcagta tatgcagcag   1260
gtaaaggaaa atactccttt agcacaccag gatcaccaac agagtagtac tggtctgggt   1320
aagatgggac gtaccccgtc gatgcagcgc gttgccagct tggagcatct gcagaagcgc   1380
atccggagcg gcgtgacttg caacactccc tccgggaaca gctactggga gatggagggc   1440
ccagccatgg tggaacaaca tgacatctaa acaattgatt tcttaagagt ttcgttttta   1500
ctaagtttgt tattataatt gtgtttaaac tatattgctg tgactcactc cacgacgcca   1560
atgctaactg atgacgagag ctcgcaaggg c                                  1591
```

<210> SEQ ID NO 3
<211> LENGTH: 469
<212> TYPE: PRT
<213> ORGANISM: Physcomitrella patens

<400> SEQUENCE: 3

```
Met Glu His Ser Ser Val Asp Asp Leu Val Gly Thr Phe Trp Asp
  1               5                  10                  15

Asp Ser Ala Asp Leu Val Asp Lys Ala Ala Ser Thr Thr Ile Asn
                 20                  25                  30

Arg Ser Ala Ser Glu Trp Ser Phe Gln Glu Phe Leu Lys Asp Ser His
         35                  40                  45

Ser Ala Ala Ala Gly Pro Gly Ala Leu Lys Leu Arg Pro Ala Cys Lys
     50                  55                  60

Ser Arg Phe Leu Met Glu His Gly Asp Val Lys Val Cys Glu Pro Glu
 65                  70                  75                  80

Ala Gln Lys Val Lys Glu Ser Leu Arg Ala Glu Glu Asp Val Gly
                 85                  90                  95

Glu Glu Pro Tyr Ile Ser Ala Ala Glu Leu Arg Leu Tyr Pro His Ser
            100                 105                 110

Gly Ser Ser Asp Phe Ser Ala Pro Met Gly Thr Ser Glu Glu Leu Gln
        115                 120                 125

Val Val Asp Asp Asn Asp Pro Ser Val Val Glu Gly Ala Leu Asn
            130                 135                 140

Pro Leu Phe Ser Gly Met Arg Asp Asp Asn Glu Ala Ile Thr Ala His
145                 150                 155                 160

Ala Arg Ile Ala Gly Asn Pro Val Ala Pro Asp Thr Leu Asp Gly Val
                165                 170                 175

Arg Tyr Pro Gln Glu Tyr Glu Tyr Ile Leu Lys His Lys Leu Glu Met
            180                 185                 190

Ala Cys Ala Ala Val Ala Met Thr Arg Ala Lys Ala Arg Gln Thr Arg
        195                 200                 205
```

Gly Ser Ala Glu Ala Ser Val Gly Arg Ala Glu Pro Ser Pro Lys Ile
    210                 215                 220

Gln Ala Ser Gly Thr Leu Pro Pro Lys Gly Lys Thr Ser Ala Cys Asn
225                 230                 235                 240

Leu Pro Ala Ala Glu Lys Ser Asp Ala Asp Val Gly Lys Ser Arg Pro
                245                 250                 255

Ile Thr Ser Gly Ser Glu Val Ser Glu Asp Glu His Asp Glu Gln
            260                 265                 270

Asn Gly Lys Thr Ala Pro Gly Asp Ile Lys Arg Val Lys Arg Met Leu
        275                 280                 285

Ser Asn Arg Glu Ser Ala Arg Arg Ser Arg Arg Lys Gln Ala His
    290                 295                 300

Leu Ser Glu Leu Glu Met Gln Val Ala Gln Leu Arg Val Glu Asn Thr
305                 310                 315                 320

Asn Leu Leu Gln Arg Leu Gln Asp Ile Ser Gln Lys Phe Gln Glu Ala
                325                 330                 335

Ala Ile Asp Asn Arg Val Leu Thr Ala Asp Cys Glu Ala Leu Arg Ala
            340                 345                 350

Lys Val Asn Met Ala Ala Arg Asp Leu Met Ala Arg His Gly Gln Ile
        355                 360                 365

Pro Gly Gly Gln Phe Ile Leu Glu Pro Ser Leu Arg Tyr Val Leu Pro
    370                 375                 380

Tyr Glu Met Gln Pro Val Ala Asp Glu Ser Ala Gln Tyr Met Gln Gln
385                 390                 395                 400

Val Lys Glu Asn Thr Pro Leu Ala His Gln Asp His Gln Ser Ser
                405                 410                 415

Thr Gly Leu Gly Lys Met Gly Arg Thr Pro Ser Met Gln Arg Val Ala
            420                 425                 430

Ser Leu Glu His Leu Gln Lys Arg Ile Arg Ser Gly Val Thr Cys Asn
        435                 440                 445

Thr Pro Ser Gly Asn Ser Tyr Trp Glu Met Glu Gly Pro Ala Met Val
450                 455                 460

Glu Gln His Asp Ile
465

<210> SEQ ID NO 4
<211> LENGTH: 738
<212> TYPE: DNA
<213> ORGANISM: Physcomitrella patens

<400> SEQUENCE: 4
gcacgagcca aaatgatgcg ataaaaaat attccaattt cccctctgct gcgttatctg    60
cgggtgactg tggtggtcaa gactatgagg acatccttaa gcagaagttg aaagggcgt   120 gcgctgcagc ggctctctct agagtgaatg cgagggtgc aataatcggc accagatcgg   180
ttggagctat tgtcagaag agttttgcta tcgaatcatc tgccgctagt gcttgtccaa   240
gtggagttca atgcgcaccc atgagcgcta agtctccttc tccaaaacct gaagtggatg   300
catcaaccgg gaaggtcaaa cttacgacca gtggttcgga actttctgat gacgacgaac   360
atgatttgtt aaaccaaagc ctaccaggcg gtgaccttaa gcgtgtgaag agaatgttgt   420
caaaccgtga atctgcccga cgctcgcgca gaaggaaaca ggcacacttg agtgatctag   480
aaatgcaggt tgcgcaattg cgagttgaaa atactacgct tatgcaaaga ttgcaagaga   540
ttacccacat gcataaagat gcatctgtcg acaaccgaat tctaaaggca gatgtggagg   600

-continued

```
cgttgcgtgc taaggtgaaa atggctgaag acatggtggc ccgtcaagga cagcccatgt    660
caaatctcat tcccgaccca gtttaagctt tatgacaccg ttcaatgtga atgatatgga    720
aagaccattt ctgcaaca                                                   738
```

<210> SEQ ID NO 5
<211> LENGTH: 1465
<212> TYPE: DNA
<213> ORGANISM: Physcomitrella patens

<400> SEQUENCE: 5

```
atcccgggag ttcctccaca tttcccgaca atctattttt ctttagaata tggatcgcat     60
atcttccgtt gacgacatcc tgagcgcata ctggaacgag tcgtctatga cttctcctgt    120
gaagggcagc atgaaccgca gtgcttctga gttcgctttt caagaattta ttaaggagaa    180
catgactgcc acatcttgct tcggaggccg ctccaagagc cgcttctatc aatcgcaggc    240
ggatgagggg aaagctctta acgatcaaag tcgtgacaat cttatgatct cggcaaaatc    300
tgaatcagag ttcactcctc cgatgttcgc aagcaccgag gagctgcgtg cgatgaataa    360
cgtcgtggac cctgttgaag tcgacgatat tgtggggatt gagggggcgc tgaaccccct    420
cttctcccgt gtccaaaatg atgcggataa aaaatattcc aatttcccct ctgctgcgtt    480
atctgcgggt gactgtggtg gtcaagacta tgaggacatc cttaagcaga gttgggaag    540
ggcgtgcgct gcagcggctc tctctagagt gaatggcgag ggtgcaataa ttggacaatc    600
ggttggagct atttgtcaga agagttttgc tatcgaatca tctgccgcta gtgcttgtcc    660
aagtggagtt caatgcgcac ccatgagcgc taagtctcct tctccaaaac ctgaagtgga    720
tgcatcaacc gggaaggtca aacttacgac cagtggttcg gaacttctg atgacgacga    780
acatgatttg ttaaaccaaa gcctaccagg cggtgacctt aagcgtgtga agagaatgtt    840
gtcaaaccgt gaatctgccc gacgctcgcg cagaaggaaa caggcacact tgagtgatct    900
agaaatgcag gttgcgcaat tgcgagttga aaatactacg cttatgcaaa gattgcaaga    960
gattacccac atgcataaag atgcatctgt cgacaaccga attctaaagg cagatgtgga   1020
ggcgttgcgt gctaaggtga aaatggctga agacatggtg gcccgtcaag gacagcccat   1080
gtcaaatctc attcccgacc ccagtttaag ctttatgaca ccgttcaatg tgaatgatat   1140
ggaaagacca tttctgcaac agatgaggca gttccatg ctacgccatg atcagcaaca   1200
gcagcctgct agtggcatta ggggtaagat gggacgtgca ccttcaatgc aacgggttgc   1260
cagcctggag catctgacga agcgtatccg caacggagt tcctgcaacg taccggcttg   1320
gggtggctgg gacatggaca gacctgccat ggtacaggaa cacggcatct gatcaatgtt   1380
tccgcgctga ctatgtagta gaatcgatgt aacttacatt tactccgctt atttcaagcg   1440
agagcgaggt tcagggcgag ctcgc                                        1465
```

<210> SEQ ID NO 6
<211> LENGTH: 440
<212> TYPE: PRT
<213> ORGANISM: Physcomitrella patens

<400> SEQUENCE: 6

```
Met Asp Arg Ile Ser Ser Val Asp Asp Ile Leu Ser Ala Tyr Trp Asn
 1               5                  10                  15
Glu Ser Ser Met Thr Ser Pro Val Lys Gly Ser Met Asn Arg Ser Ala
            20                  25                  30
```

```
Ser Glu Phe Ala Phe Gln Glu Phe Ile Lys Glu Asn Met Thr Ala Thr
         35                  40                  45

Ser Cys Phe Gly Gly Arg Ser Lys Ser Arg Phe Tyr Gln Ser Gln Ala
         50                  55                  60

Asp Glu Gly Lys Ala Leu Asn Asp Gln Ser Arg Asp Asn Leu Met Ile
 65                  70                  75                  80

Ser Ala Lys Ser Glu Ser Glu Phe Thr Pro Pro Met Phe Ala Ser Thr
                 85                  90                  95

Glu Glu Leu Arg Ala Met Asn Asn Val Val Asp Pro Val Glu Val Asp
            100                 105                 110

Asp Ile Val Gly Ile Glu Gly Ala Leu Asn Pro Leu Phe Ser Arg Val
            115                 120                 125

Gln Asn Asp Ala Asp Lys Lys Tyr Ser Asn Phe Pro Ser Ala Ala Leu
        130                 135                 140

Ser Ala Gly Asp Cys Gly Gly Gln Asp Tyr Glu Asp Ile Leu Lys Gln
145                 150                 155                 160

Lys Leu Gly Arg Ala Cys Ala Ala Ala Leu Ser Arg Val Asn Gly
                165                 170                 175

Glu Gly Ala Ile Ile Gly Gln Ser Val Gly Ala Ile Cys Gln Lys Ser
            180                 185                 190

Phe Ala Ile Glu Ser Ser Ala Ala Ser Ala Cys Pro Ser Gly Val Gln
            195                 200                 205

Cys Ala Pro Met Ser Ala Lys Ser Pro Ser Pro Lys Pro Glu Val Asp
            210                 215                 220

Ala Ser Thr Gly Lys Val Lys Leu Thr Thr Ser Gly Ser Glu Leu Ser
225                 230                 235                 240

Asp Asp Asp Glu His Asp Leu Leu Asn Gln Ser Leu Pro Gly Gly Asp
                245                 250                 255

Leu Lys Arg Val Lys Arg Met Leu Ser Asn Arg Glu Ser Ala Arg Arg
            260                 265                 270

Ser Arg Arg Arg Lys Gln Ala His Leu Ser Asp Leu Glu Met Gln Val
        275                 280                 285

Ala Gln Leu Arg Val Glu Asn Thr Thr Leu Met Gln Arg Leu Gln Glu
        290                 295                 300

Ile Thr His Met His Lys Asp Ala Ser Val Asp Asn Arg Ile Leu Lys
305                 310                 315                 320

Ala Asp Val Glu Ala Leu Arg Ala Lys Val Lys Met Ala Glu Asp Met
                325                 330                 335

Val Ala Arg Gln Gly Gln Pro Met Ser Asn Leu Ile Pro Asp Pro Ser
            340                 345                 350

Leu Ser Phe Met Thr Pro Phe Asn Val Asn Asp Met Glu Arg Pro Phe
        355                 360                 365

Leu Gln Gln Met Arg His Ser Ser Met Leu Arg His Asp Gln Gln Gln
        370                 375                 380

Gln Pro Ala Ser Gly Ile Arg Gly Lys Met Gly Arg Ala Pro Ser Met
385                 390                 395                 400

Gln Arg Val Ala Ser Leu Glu His Leu Thr Lys Arg Ile Arg Asn Gly
                405                 410                 415

Ser Ser Cys Asn Val Pro Ala Trp Gly Gly Trp Asp Met Asp Arg Pro
            420                 425                 430

Ala Met Val Gln Glu His Gly Ile
            435                 440
```

<210> SEQ ID NO 7
<211> LENGTH: 756
<212> TYPE: DNA
<213> ORGANISM: Physcomitrella patens

<400> SEQUENCE: 7

| | | |
|---|---|---|
| taccttctga atgcatcgtc acgtctgttc tctttccagg cctgatagcg aagcgcaact | 60 |
| tctggcagct gtatgagcag cagccagtac atcgcggcac gaccagttac aggtccttcg | 120 |
| ctaagaacat gggtgtgtgc aacgacggct ataaaaccat caacatggca gcctagatct | 180 |
| attttgacaa tgtcatttgc tgcaagaaca gattcgtcgc tggccaaagg cgagaagtgg | 240 |
| catacggtgt tgttgacaga gacacaagtg ggaaatgcaa ctcccttgtc aattttttc | 300 |
| ttggagttct tgtacatgag cgctgttaga tcgcgaatcg aagaatcgcc cttctcgcaa | 360 |
| aggtcgacga tcttcgctcc tggcttgcaa tcggccagga ctgcttgcaa ggccttgtta | 420 |
| gcgacctcgg ccgcgcactt atacttggtg acgacatccg cgacgtcaa gtcgagctcc | 480 |
| ttctcctctt tcacctcatc atccgacatc gcgtcacgcg ggtttcaaaa caaaaccgag | 540 |
| ctcctctcaa ctcctgaccc tcactgcctt gaacaggtag aaaacgcagc tcagtcacct | 600 |
| caacacggct ctgagcaatg cgcaagacga aaaaaaatc tacaactgag gccaccgtgt | 660 |
| agcagagcaa aagaggggt gtccgagaac gctcgtgcca gggaacgaca gacaacgatg | 720 |
| cagggctcc gccgaggact tgtgtcaagc tggtgc | 756 |

<210> SEQ ID NO 8
<211> LENGTH: 1641
<212> TYPE: DNA
<213> ORGANISM: Physcomitrella patens

<400> SEQUENCE: 8

| | | |
|---|---|---|
| ggcaccagca cccctctctt tgctctgcta cacggtggcc tcagttgtag attttttttt | 60 |
| cgtcttgcgc attgctcaga gccgtgttga ggtgactgag ctgcgttttc tacctgttca | 120 |
| aggcagtgag ggtcaggagt tgagaggagc tcggttttgt tttgaaaccc gcgtgacgcg | 180 |
| atgtcggatg atgaggtgaa agaggagaag gagctcgact tgacgtcgcc ggatgtcgtc | 240 |
| accaagtata agtgcgcggc cgaggtcgct aacaaggcct tgcaagcagt cctggccgat | 300 |
| tgcaagccag gagcgaagat cgtcgacctt tgcgagaagg gcgattcttc gattcgcgat | 360 |
| ctaacagcgc tcatgtacaa gaactccaag aaaaaaattg acaagggagt tgcatttccc | 420 |
| acttgtgtct ctgtcaacaa caccgtatgc cacttctcgc cttttggccag cgacgaatct | 480 |
| gttcttgcag caaatgacat tgtcaaaata gatctaggct gccatgttga tggttttata | 540 |
| gccgtcgttg cacacaccca tgttcttagc gaaggacctg taactggtcg tgccgcggat | 600 |
| gttctggctg ctgctcatac agctgcagaa gttgcgcttc gcctagtcag gcctggaaag | 660 |
| aagaacaagg acgtgaccga tgcaattcag aaggtagcgg ctgcctacga ttgcaagatt | 720 |
| gccgagggtg tgttgagtca tcagctcaag cagtttgtca tcgatgctaa caaagtaatc | 780 |
| ctgagtgtat cgaaccctga aacgcgtgta atgatgccg agttcgagga aaacgaggtc | 840 |
| tatgcaattg acatcgtgac cagtacgggt gatggaaagc ccaagttgtt agatgagaag | 900 |
| cagaccacag tgtataagag ggctgtggac aagaattatc acctgaaaat gaaggcatca | 960 |
| agattcatct tcagcgaaat caataccaag ttccctatta tgcctttcac tgctagagct | 1020 |
| ctagaagaga gagggcccg ccttggtatc gtggagtgtg ttaaccatga actgcttcag | 1080 |
| ccctaccctg ttcttcacga aaagcccggt gactgcgtag cccacattaa gttcactgta | 1140 |

-continued

```
ttgctcatgc ccaacggatc cgataagata actggtctgc cacttcaaga atgtcagtcg    1200
accaaagttc ccgaggaccc agagatcaaa gcttggttgg ctttgggtac taagtccaaa    1260
aagaagggtg gtggtaagaa gaaaaaaggt aagaaaggcg acgccatgat tgaggactcg    1320
tctgaaacag ccgcagagtc agccacagga actactgata caatggacac ttcagcctag    1380
acttcacaga acagagtgga ttgagagtcg tacccatgca ccatttcacg aaccctaaac    1440
tccgtgcagt ctaagttcca tctctggtgc tcatattcgt gcaccatttc agttttgctc    1500
ctgactctag cgatagtcct gtctggtaac catacaacct attggacata tcccgacaat    1560
gctgttgctt gttcaaatcc ctgtgctcca tcaagatgaa agctctttt taaaacccaa     1620 aaaaaaaaaa aaaaaaaaa a                                               1641
```

<210> SEQ ID NO 9
<211> LENGTH: 399
<212> TYPE: PRT
<213> ORGANISM: Physcomitrella patens

<400> SEQUENCE: 9

Met Ser Asp Asp Glu Val Lys Glu Lys Glu Leu Asp Leu Thr Ser
1               5                   10                  15

Pro Asp Val Val Thr Lys Tyr Lys Cys Ala Ala Glu Val Ala Asn Lys
            20                  25                  30

Ala Leu Gln Ala Val Leu Ala Asp Cys Lys Pro Gly Ala Lys Ile Val
        35                  40                  45

Asp Leu Cys Glu Lys Gly Asp Ser Ser Ile Arg Asp Leu Thr Ala Leu
    50                  55                  60

Met Tyr Lys Asn Ser Lys Lys Lys Ile Asp Lys Gly Val Ala Phe Pro
65                  70                  75                  80

Thr Cys Val Ser Val Asn Asn Thr Val Cys His Phe Ser Pro Leu Ala
                85                  90                  95

Ser Asp Glu Ser Val Leu Ala Ala Asn Asp Ile Val Lys Ile Asp Leu
            100                 105                 110

Gly Cys His Val Asp Gly Phe Ile Ala Val Val Ala His Thr His Val
        115                 120                 125

Leu Ser Glu Gly Pro Val Thr Gly Arg Ala Ala Asp Val Leu Ala Ala
    130                 135                 140

Ala His Thr Ala Ala Glu Val Ala Leu Arg Leu Val Arg Pro Gly Lys
145                 150                 155                 160

Lys Asn Lys Asp Val Thr Asp Ala Ile Gln Lys Val Ala Ala Ala Tyr
                165                 170                 175

Asp Cys Lys Ile Ala Glu Gly Val Leu Ser His Gln Leu Lys Gln Phe
            180                 185                 190

Val Ile Asp Ala Asn Lys Val Ile Leu Ser Val Ser Asn Pro Glu Thr
        195                 200                 205

Arg Val Asp Asp Ala Glu Phe Glu Glu Asn Glu Val Tyr Ala Ile Asp
    210                 215                 220

Ile Val Thr Ser Thr Gly Asp Gly Lys Pro Lys Leu Leu Asp Glu Lys
225                 230                 235                 240

Gln Thr Thr Val Tyr Lys Arg Ala Val Asp Lys Asn Tyr His Leu Lys
                245                 250                 255

Met Lys Ala Ser Arg Phe Ile Phe Ser Glu Ile Asn Thr Lys Phe Pro
            260                 265                 270

Ile Met Pro Phe Thr Ala Arg Ala Leu Glu Glu Lys Arg Ala Arg Leu
        275                 280                 285

```
Gly Ile Val Glu Cys Val Asn His Glu Leu Leu Gln Pro Tyr Pro Val
    290                 295                 300

Leu His Glu Lys Pro Gly Asp Cys Val Ala His Ile Lys Phe Thr Val
305                 310                 315                 320

Leu Leu Met Pro Asn Gly Ser Asp Lys Ile Thr Gly Leu Pro Leu Gln
                325                 330                 335

Glu Cys Gln Ser Thr Lys Val Pro Glu Asp Pro Glu Ile Lys Ala Trp
            340                 345                 350

Leu Ala Leu Gly Thr Lys Ser Lys Lys Gly Gly Lys Lys
            355                 360                 365

Lys Gly Lys Lys Gly Asp Ala Met Ile Glu Asp Ser Ser Glu Thr Ala
    370                 375                 380

Ala Glu Ser Ala Thr Gly Thr Thr Asp Thr Met Asp Thr Ser Ala
385                 390                 395
```

<210> SEQ ID NO 10
<211> LENGTH: 670
<212> TYPE: DNA
<213> ORGANISM: Physcomitrella patens

<400> SEQUENCE: 10

```
cggcaccaga aaatggttgc cgagagtgtg ttggtgtgta ggagcagtgt cgtcggggct    60
ggattgcaga gctttgttgg agagggcgcg aagagagagt cagcagggcc agggagaagc   120
gtgttttttgg gagctcaggt gcagaagatg ggagcgggta tgtccgcgcg gtcggatgtg   180
cgacctgcag cagttccgaa agcttcagga gatgtcagtg agcagactga ctataaaaca   240
ttcagtgatg aggaatggaa gaagcgtctg tctcaacagc aattctacgt cgcacgcaag   300
aaaggcaccg aaagaccttt cactggagag tactggaaca ccaaaacagc aggaacatac   360
ctatgcgttt gttgtaagac accattgttc agctcaaaga ccaagttcga cagtggtacc   420
ggatggccat cttactatga caccataggt gacaatgtga agtcacacat ggattggtcg   480
ataccttca tgccccgcac tgaggttgtg tgtgctgtgt gcgatgctca tctgggtcat   540
gtcttcgacg atgggccgag gcctactggc aaacgttatt gtatcaacag cgcggcgatt   600
gatttgaagg ccgaaagcag aagagaggga ctagtacgtc agggtttgga aggggggaat   660
ggaaatcaat                                                          670
```

<210> SEQ ID NO 11
<211> LENGTH: 648
<212> TYPE: DNA
<213> ORGANISM: Physcomitrella patens

<400> SEQUENCE: 11

```
atcccgggag aaaatggttg ccgagagtgt gttggtgtgt aggagcagtg tcgtcggggc    60
tggattgcag agctttgttg gagagggcgc gaagagagag tcagcagggc agggagaag   120
cgtgtttttg ggagctcagg tgcagaagat gggagcgggt atgtccgcgc ggtcggatgt   180
gcgacctgca gcagttccga aagcttcagg agatgtcagt gagcagactg actataaaac   240
attcagtgat gaggaatgga agaagcgtct gtctcaacag caattctacg tcgcacgcaa   300
gaaaggcacc gaaagacctt tcactggaga gtactggaac accaaaacag caggaacata   360
cctatgcgtt tgttgtaaga caccattgtt cagctcaaag accaagttcg acagtggtac   420
cggatggcca tcttactatg acaccatagg tgacaatgtg aagtcacaca tggattggtc   480
gataccttc atgccccgca ctgaggttgt gtgtgctgtg tgcgatgctc atctgggtca   540
```

```
tgtcttcgac gatgggccga ggcctactgg caaacgttat tgtatcaaca gcgcggcgat    600
tgatttgaag gccgagaagc aagaagagag gaactaggta gatatcag                 648
```

<210> SEQ ID NO 12
<211> LENGTH: 207
<212> TYPE: PRT
<213> ORGANISM: Physcomitrella patens

<400> SEQUENCE: 12

```
Met Val Ala Glu Ser Val Leu Val Cys Arg Ser Ser Val Val Gly Ala
 1               5                  10                  15

Gly Leu Gln Ser Phe Val Gly Glu Gly Ala Lys Arg Glu Ser Ala Gly
            20                  25                  30

Pro Gly Arg Ser Val Phe Leu Gly Ala Gln Val Gln Lys Met Gly Ala
        35                  40                  45

Gly Met Ser Ala Arg Ser Asp Val Arg Pro Ala Val Pro Lys Ala
    50                  55                  60

Ser Gly Asp Val Ser Glu Gln Thr Asp Tyr Lys Thr Phe Ser Asp Glu
65                  70                  75                  80

Glu Trp Lys Lys Arg Leu Ser Gln Gln Gln Phe Tyr Val Ala Arg Lys
                85                  90                  95

Lys Gly Thr Glu Arg Pro Phe Thr Gly Glu Tyr Trp Asn Thr Lys Thr
            100                 105                 110

Ala Gly Thr Tyr Leu Cys Val Cys Cys Lys Thr Pro Leu Phe Ser Ser
        115                 120                 125

Lys Thr Lys Phe Asp Ser Gly Thr Gly Trp Pro Ser Tyr Tyr Asp Thr
    130                 135                 140

Ile Gly Asp Asn Val Lys Ser His Met Asp Trp Ser Ile Pro Phe Met
145                 150                 155                 160

Pro Arg Thr Glu Val Val Cys Ala Val Cys Asp Ala His Leu Gly His
                165                 170                 175

Val Phe Asp Asp Gly Pro Arg Pro Thr Gly Lys Arg Tyr Cys Ile Asn
            180                 185                 190

Ser Ala Ala Ile Asp Leu Lys Ala Glu Lys Gln Glu Glu Arg Asn
        195                 200                 205
```

<210> SEQ ID NO 13
<211> LENGTH: 822
<212> TYPE: DNA
<213> ORGANISM: Brassica napus

<400> SEQUENCE: 13

```
cgaagaacga aagagataaa agagcaacaa tggcgttgaa cgtcatctca tcatcatctt    60
cagccacttc catttccatg acctttgctt ccaccatcag agccttcgtt agaccttctc   120
tctccctcag aaccactcca tttgctcgct tccgtcgaa gcttaacctc cttcctctcc    180
ccgcctctcc ttcatcattt cctccgctcc gtcttcgtag ccgaggcttc acggtggtc    240 gtgtcacagc aatgtcttct cctgctcccg gatcggtgaa taagccagag aagaatggc    300 gtgcgattct gtctcctgag caattcagga tcctgaggca gaaggcacc gaatatccag    360 gaacaggaga atacaacaaa ctattcgaag acggcatcta ttcatgtgca ggatgtggga    420
ctcctcttta caaatccgcc accaaattcg actccggttg tggctggcca gctttctttg    480
acggccttcc cggtgctata aaccgaactc ctgatccaga tgggagaaga atcgagatca    540
cttgtgcggc ttgtgggga catctcggcc atgttttcaa aggagaaggt ttccctacac    600
```

```
ctaccgatga gcgacactgt gtgaacagtg tttctctcaa gttcgcacca gggaatcaag    660
acttgtaata atgttcttgg tgttgtgtaa tgcttctgtc tatgtcttgt gtgtcctgct    720
cgttataacc agtgtttagt tccattaatg tcgttgaatc aaaaaaaaaa aaaaaaaaa    780 aaaaaaaaaa aaaaaaaaa aaaaaaaaa aaaaaaaaa aa                         822
```

<210> SEQ ID NO 14
<211> LENGTH: 212
<212> TYPE: PRT
<213> ORGANISM: Brassica napus

<400> SEQUENCE: 14

```
Met Ala Leu Asn Val Ile Ser Ser Ser Ala Thr Ser Ile Ser
 1               5                  10                  15

Met Thr Phe Ala Ser Thr Ile Arg Ala Phe Val Arg Pro Ser Leu Ser
                20                  25                  30

Leu Arg Thr Thr Pro Phe Ala Arg Ser Pro Ser Lys Leu Asn Leu Leu
            35                  40                  45

Pro Leu Pro Ala Ser Pro Ser Ser Phe Pro Pro Leu Arg Leu Arg Ser
        50                  55                  60

Arg Gly Phe His Gly Gly Arg Val Thr Ala Met Ser Ser Pro Ala Pro
65                  70                  75                  80

Gly Ser Val Asn Lys Pro Glu Glu Glu Trp Arg Ala Ile Leu Ser Pro
                85                  90                  95

Glu Gln Phe Arg Ile Leu Arg Gln Lys Gly Thr Glu Tyr Pro Gly Thr
            100                 105                 110

Gly Glu Tyr Asn Lys Leu Phe Glu Asp Gly Ile Tyr Ser Cys Ala Gly
        115                 120                 125

Cys Gly Thr Pro Leu Tyr Lys Ser Ala Thr Lys Phe Asp Ser Gly Cys
    130                 135                 140

Gly Trp Pro Ala Phe Phe Asp Gly Leu Pro Gly Ala Ile Asn Arg Thr
145                 150                 155                 160

Pro Asp Pro Asp Gly Arg Arg Ile Glu Ile Thr Cys Ala Ala Cys Gly
                165                 170                 175

Gly His Leu Gly His Val Phe Lys Gly Glu Gly Phe Pro Thr Pro Thr
            180                 185                 190

Asp Glu Arg His Cys Val Asn Ser Val Ser Leu Lys Phe Ala Pro Gly
        195                 200                 205

Asn Gln Asp Leu
    210
```

<210> SEQ ID NO 15
<211> LENGTH: 813
<212> TYPE: DNA
<213> ORGANISM: Oryza sativa

<400> SEQUENCE: 15

```
ccgaagaaaa tggccatgcg gcaatacgcg gctgctaccg ctgcctcctc cagtttcaga     60
gcacgtccac gggcgcgccc ctcctgcctc ccagccgccg ccctgcccTt ggcgccttgc    120
tgtggtgtgg cgtggagccg tgctagctac aggcgagcct ccgttcgtgc catgggtgcc    180
gcttcatcgt cttcgtcgtc gtcgtcgtcg tctccgtcgc cgcagggtca agcccaagcc    240
caagcccaag gtaaaccgaa ctacagtaca tctctgactg atgaggagtg gaggaagcgc    300
ctgacaaaag atcagtatta cattactcgg cagaagggca gaaagagc atttactggg     360
```

```
gaatactgga acaccaaaac cccgggcatc taccattgtg tctgctgtga caccctctt     420 tttgagtcat cgaccaaatt tgatagtggt actgggtggc cgtcatatta tcaacccatt   480
ggagataatg taaagtgcaa gcttgatatg tccatcatat tcatgcctcg gactgaggtg   540
ctgtgtgctg tctgtgacgc tcatctgggg cacgtgtttg atgatgggcc acgaccaaca   600
gggaaaagat actgtatcaa tagcgcatct ctcaagctga agaaccca gtagacctgt     660 gaagattatg gttaccatgt acctacacgg ctacactatc cgactagtta taagggatag   720
attatgtata tagaatatgt aaagaattaa gacttgggta ttatgtttac ttgtgtatca   780
agaaaaaaaa aaaaaaaaaa aaaaaaaaaa aaa                                 813
```

<210> SEQ ID NO 16
<211> LENGTH: 214
<212> TYPE: PRT
<213> ORGANISM: Oryza sativa

<400> SEQUENCE: 16

```
Met Ala Met Arg Gln Tyr Ala Ala Ala Thr Ala Ala Ser Ser Ser Phe
 1               5                  10                  15

Arg Ala Arg Pro Arg Ala Arg Pro Ser Cys Leu Pro Ala Ala Ala Leu
            20                  25                  30

Pro Leu Ala Pro Cys Cys Gly Val Ala Trp Ser Arg Ala Ser Tyr Arg
        35                  40                  45

Arg Ala Ser Val Arg Ala Met Gly Ala Ala Ser Ser Ser Ser Ser Ser
    50                  55                  60

Ser Ser Ser Ser Pro Ser Pro Gln Gly Gln Ala Gln Ala Gln Ala Gln
65                  70                  75                  80

Gly Lys Pro Asn Tyr Ser Thr Ser Leu Thr Asp Glu Glu Trp Arg Lys
                85                  90                  95

Arg Leu Thr Lys Asp Gln Tyr Tyr Ile Thr Arg Gln Lys Gly Thr Glu
            100                 105                 110

Arg Ala Phe Thr Gly Glu Tyr Trp Asn Thr Lys Thr Pro Gly Ile Tyr
        115                 120                 125

His Cys Val Cys Cys Asp Thr Pro Leu Phe Glu Ser Ser Thr Lys Phe
    130                 135                 140

Asp Ser Gly Thr Gly Trp Pro Ser Tyr Tyr Gln Pro Ile Gly Asp Asn
145                 150                 155                 160

Val Lys Cys Lys Leu Asp Met Ser Ile Ile Phe Met Pro Arg Thr Glu
                165                 170                 175

Val Leu Cys Ala Val Cys Asp Ala His Leu Gly His Val Phe Asp Asp
            180                 185                 190

Gly Pro Arg Pro Thr Gly Lys Arg Tyr Cys Ile Asn Ser Ala Ser Leu
        195                 200                 205

Lys Leu Lys Lys Thr Gln
    210
```

<210> SEQ ID NO 17
<211> LENGTH: 785
<212> TYPE: DNA
<213> ORGANISM: Oryza sativa

<400> SEQUENCE: 17

```
gtgacccgtg attcgtgaac acaaacacca tcgccatggg cttcaatatt ctgagaacca    60
cttccatctc cactcctatc tcttcctcca atccaaaacc catttttctca actcttcttc   120 gttcttctcc ttccaccatt ttccccccaa agtccgttac tccaccact cttttcgttt    180
```

```
ctgccacccc cttcttcact ctccatccca agcttggttt tcgtggtggg attgtggcca    240
tggccgcacc tggctctctc cgcaaatccg aggaagagtg gcgcgcaatt ctctcccctg    300
aacagtttcg gatcctcagg caaaagggca ccgagttccc tggaacagga gagtatgaca    360
agttctatga agagggagtt tacaactgtg ctggttgtgg gactccactc tacaggtcca    420
taacaaaatt caattctggt tgtggctggc cagccttcta tgagggatt  cccgagcca     480 taaatcgcaa tccggatcct gatgggatga ggacagaaat aacgtgtgct gcttgtgggg    540
gacatctagg tcacgtcttt aaaggagaag gatttccaac acccactaac gaacgccatt    600
gtgtcaatag catttcgctg aaatttgcgc cagccaattc ttattcttaa taaaattgag    660
tctgctgttt ggacgtgact acttaagtac ccaacatcgg taaaaaaatt atgcaatgta    720
cttatattat gaatgaagtt aaaaaaaaaa tgatggagag agagagaccg acacgcagcg    780
gccgc                                                                 785
```

<210> SEQ ID NO 18
<211> LENGTH: 204
<212> TYPE: PRT
<213> ORGANISM: Oryza sativa

<400> SEQUENCE: 18

```
Met Gly Phe Asn Ile Leu Arg Thr Thr Ser Ile Ser Thr Pro Ile Ser
 1               5                   10                  15

Ser Ser Lys Ser Lys Pro Ile Phe Ser Thr Leu Leu Arg Ser Ser Pro
            20                  25                  30

Ser Thr Ile Phe Pro Pro Lys Ser Val Thr Pro Thr Thr Leu Phe Val
        35                  40                  45

Ser Ala Thr Pro Phe Phe Thr Leu His Pro Lys Leu Gly Phe Arg Gly
    50                  55                  60

Gly Ile Val Ala Met Ala Ala Pro Gly Ser Leu Arg Lys Ser Glu Glu
65                  70                  75                  80

Glu Trp Arg Ala Ile Leu Ser Pro Glu Gln Phe Arg Ile Leu Arg Gln
                85                  90                  95

Lys Gly Thr Glu Phe Pro Gly Thr Gly Glu Tyr Asp Lys Phe Tyr Glu
            100                 105                 110

Glu Gly Val Tyr Asn Cys Ala Gly Cys Gly Thr Pro Leu Tyr Arg Ser
        115                 120                 125

Ile Thr Lys Phe Asn Ser Gly Cys Gly Trp Pro Ala Phe Tyr Glu Gly
    130                 135                 140

Ile Pro Gly Ala Ile Asn Arg Asn Pro Asp Pro Asp Gly Met Arg Thr
145                 150                 155                 160

Glu Ile Thr Cys Ala Ala Cys Gly Gly His Leu Gly His Val Phe Lys
                165                 170                 175

Gly Glu Gly Phe Pro Thr Pro Thr Asn Glu Arg His Cys Val Asn Ser
            180                 185                 190

Ile Ser Leu Lys Phe Ala Pro Ala Asn Ser Tyr Ser
        195                 200
```

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 19
caggaaacag ctatgacc                                          18

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 20
ctaaagggaa caaaagctg                                         19

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21
tgtaaaacga cggccagt                                          18

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
atcccgggac gcgatgtcgg atgatgaggt ga                          32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 23
ctgatatcag tctaggctga agtgtccatt gt                          32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 24
atcccgggcg tcgcagttta cgtgtgttca cc                          32

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 25
ctgatatcta cctagttcct ctcttcttgc ttc                         33

<210> SEQ ID NO 26
<211> LENGTH: 25
<212> TYPE: DNA

```
<213> ORGANISM: Artificial Sequence
<220> FEATURE:
<223> OTHER INFORMATION: Description of Artificial Sequence: Primer

<400> SEQUENCE: 26
gcccgagtca tggcgactgc agcac                                          25

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 27
atcccgggtc aagctacgac gcctcaatct tcc                                 33

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 28
gcgagctctc gtcatcagtt agcattggcg tcgt                                34

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 29
tagcgctcat gggtgcgcat tgaac                                          25

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 30
atcccgggag ttcctccaca tttcccgaca atc                                 33

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 31
gcgagctcgc cctgaactct cgctctcgct tg                                  32

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 32
gcaccgagga gctgcgtgcg atgaa                                          25
```

```
<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 33
cgcttaaggt caccgcctgg tagg                                          24

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 34
cgccaagcgc gcaattaacc ctcact                                        26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 35
gcgtaatacg actcactata gggcga                                        26
```

TRANSCRIPTION FACTOR STRESS-RELATED POLYPEPTIDES AND METHODS OF USE IN PLANTS

CROSS-REFERENCE TO RELATED APPLICATIONS

The present invention claims the priority benefit of U.S. Provisional Patent Application Ser. No. 60/344,503 filed Nov. 9, 2001, the entire contents of which are hereby incorporated by reference.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

One model plant used in the study of stress tolerance is *Arabidopsis thaliana*. There are at least four different signal-transduction pathways leading to stress tolerance in the model plant *Arabidopsis thaliana*. These pathways are under the control of distinct transcription factors (Shinozaki et al., 2000, Curr. Opin. Plant Biol. 3:217–23). Regulators of genes, especially transcription factors, involved in these tolerance pathways are particularly suitable for engineering tolerance into plants because a single gene can activate a whole cascade of genes leading to the tolerant phenotype. Consequently, transcription factors are important targets in the quest to identify genes conferring stress tolerance to plants.

One transcription factor that has been identified in the prior art is the *Arabidopsis thaliana* transcription factor CBF (Jaglo-Ottosen et al., 1998, Science 280:104–6). Over-expression of this gene in *Arabidopsis* conferred drought tolerance to this plant (Kasuga et al., 1999, Nature Biotech. 17:287–91). However, CBF is the only example to date of a transcription factor able to confer drought tolerance to plants upon over-expression.

An additional major type of environmental stress is lodging, which refers to the bending of shoots or stems in response to wind, rain, pests, or disease. Two types of lodging occur in cereals: root-lodging and stem breakage. The most common type of lodging is root lodging, which occurs early in the season. Stem-breakage, by comparison, occurs later in the season as the stalk becomes more brittle due to crop maturation. Stem breakage has greater adverse consequences on crop yield, since the plants cannot recover as well as from the earlier root-lodging.

Lodging in cereal crops is influenced by morphological (structural) plant traits as well as environmental conditions. Lodging in cereals is often a result of the combined effects of inadequate standing power of the crop and adverse weather conditions, such as rain, wind, and/or hail. Lodging is also variety (cultivar) dependent. For example, a tall, weak-stemmed wheat cultivar has a greater tendency to lodge than a semi-dwarf cultivar with stiffer straw. In addition, the tendency of a crop to lodge depends on the resistance especially of the lower internodes. This is because the lower internodes have to resist the greatest movement of force. The weight of the higher internodes of the stems plus leaves and heads in relation to the stem (culm) will affect the resistance of a crop to lodging. The heavier the higher parts of the stem are and the greater the distance from their center of gravity to the base of the stem, the greater is the movement of the forces acting upon the lower internodes and the roots. Supporting this argument, it was found that the breaking strength of the lowest internode and shoot per root ratio were the most suitable indices of lodging. Furthermore, plant morphological (structural) characteristics such as plant height, wall thickness, and cell wall lignification can affect the ability of the plant to resist a lateral force.

Severe lodging is very costly due to its effects on grain formation and associated harvesting problems and losses. It takes about twice the time to harvest a lodged crop than a standing one. Secondary growth in combination with a flattened crop makes harvesting difficult and can subsequently lead to poor grain quality. Yield loss comes from poor grain filling, head loss, and bird damage. Yield losses are most severe when a crop lodges during the ten days following head emergence. Yield losses at this stage will range between 15% and 40%. Lodging that occurs after the plant matures will not affect the yield but it may reduce the amount of harvestable grain. For instance, when lodging occurs after the plant matures, neck breakage and the loss of the whole head can result; these often lead to severe harvest losses. In theses cases, farmers who straight combine their grain will likely incur higher losses than those who swath them. Accordingly, it is desirable to identify genes expressed in lodging resistant plants that have the capacity to confer lodging resistance to the host plant and to other plant species.

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress tolerance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique transcription factors capable of conferring stress tolerance to plants upon over-expression. The present invention provides a transgenic plant cell transformed by a Transcription Factor Stress-Related Protein (TFSRP) coding nucleic acid, wherein expression of the nucleic acid sequence in the plant cell results in increased tolerance to environmental stress as compared to a wild type variety of the plant cell. Namely, described herein are the transcription factors 1) Leucine Zipper-2 (LZ-2); 2) Leucine Zipper-3 (LZ-3); 3) 1DNA-Binding Factor-2 (DBF-2) and 4) DNA-Binding Factor-3 (DBF-3) from *Physcomitrella patens;* 5) *Brassica napus* DNA Binding Factor-1 (BnDBF-1) from *Brassica napus*; and 6) *Oryza sativa* DNA Binding Factor-1 (OsDBF-1) and 7) *Oryza sativa* DNA Binding Factor-2 (OsDBF-2) from *Oryza sativa*.

The invention provides in some embodiments that the TFSRP and coding nucleic acid are that found in members of the genus *Physcomitrella, Brassica*, or *Oryza*. In another preferred embodiment, the nucleic acid and protein are from a *Physcomitrella patens, Brassica napus*, or an *Oryza sativa*. The invention provides that the environmental stress can be salinity, drought, temperature, metal, chemical, pathogenic, and oxidative stresses, or combinations thereof. In preferred embodiments, the environmental stress can be drought or cold temperature.

The invention further provides a seed produced by a transgenic plant transformed by a TFSRP coding nucleic acid, wherein the plant is true breeding for increased tolerance to environmental stress as compared to a wild type variety of the plant. The invention further provides a seed produced by a transgenic plant expressing and/or repressing a TFSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated TFSRP as described below. The invention further provides an isolated TFSRP coding nucleic acid, wherein the TFSRP coding nucleic acid codes for a TFSRP as described below.

The invention further provides an isolated recombinant expression vector comprising a TFSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a TFSRP coding nucleic acid, wherein expression of the nucleic acid in the plant results in increased tolerance to environmental stress as compared to a wild type variety of the plant comprising: (a) transforming a plant cell with an expression vector comprising a TFSRP coding nucleic acid, and (b) generating from the plant cell a transgenic plant with an increased tolerance to environmental stress as compared to a wild type variety of the plant. In preferred embodiments, the TFSRP and TFSRP coding nucleic acid are as described below.

The present invention also provides a method of producing a transgenic plant having an increased tolerance to environmental stress as compared to a wild type variety of the plant comprising repressing the expression of a TFSRP in the plant. In a preferred embodiment, expression of the TFSRP is repressed in the plant by the introduction of an antisense TFSRP nucleic acid. In a further preferred embodiment, the antisense TFSRP nucleic acid contains modified nucleotides to increase its stability. In preferred embodiments, the TFSRP and TFSRP coding nucleic acid are as described below.

The present invention further provides a method of identifying a novel TFSRP, comprising (a) raising a specific antibody response to a TFSRP, or fragment thereof, as described below; (b) screening putative TFSRP material with the antibody, wherein specific binding of the antibody to the material indicates the presence of a potentially novel TFSRP; and (c) identifying from the bound material a novel TFSRP in comparison to known TFSRP. Alternatively, hybridization with nucleic acid probes as described below can be used to identify novel TFSRP nucleic acids.

The present invention also provides methods of modifying stress tolerance of a plant comprising, modifying the expression of a TFSRP in the plant, wherein the TFSRP is as described below. The invention provides that this method can be performed such that the stress tolerance is either increased or decreased. Preferably, stress tolerance is increased in a plant via increasing expression of a TFSRP.

In another aspect, the invention provides methods of increasing a plant's resistance to lodging comprising, transforming a plant cell with an expression cassette comprising a TFSRP nucleic acid and generating a plant from the plant cell.

DETAILED DESCRIPTION OF THE INVENTION

Figure 1:
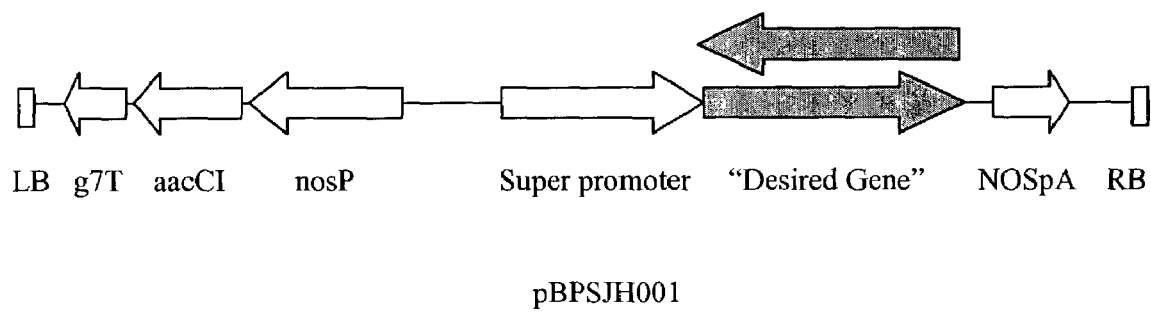
FIG. 1 shows a diagram of the plant expression vector pBPSJH001 containing the super promoter driving the expression of the TFSRP coding nucleic acid ("Desired Gene"). The components are: aacCI resistance gene (Hajdukiewicz et al., 1994, Plant Mol. Biol. 25:989–94), NOS promoter (Becker et al., 1996, Plant Mol. Biol. 20:1195–97), g7T terminator (Becker et al., 1992, supra), and NOSpA terminator (Jefferson et al., 1987, EMBO J. 6:3901–7).

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Transcription Factor Stress-Related Polypeptides" (TFSRPs), in no way limits the functionality of those sequences.

The present invention describes a novel genus of TFSRPs and TFSRP coding nucleic acids that are important for modulating a plant's response to an environmental stress. More particularly, overexpression of these TFSRP coding nucleic acids in a plant results in the plant's increased tolerance to an environmental stress.

The present invention provides a transgenic plant cell transformed by a TFSRP coding nucleic acid, wherein expression of the nucleic acid sequence in the plant cell results in increased tolerance to environmental stress or increased resistance to lodging as compared to a wild type variety of the plant cell. The invention further provides transgenic plant parts and transgenic plants containing the plant cells described herein. In preferred embodiments, the transgenic plants and plant parts have increased tolerance to environmental stress or increased resistance to lodging as compared to a wild type variety of the plant or plant part. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by a TFSRP coding nucleic acid, wherein the seed contains the TFSRP coding nucleic acid, and wherein the plant is true breeding for increased tolerance to environmental stress as compared to a wild type variety of the plant. The invention further provides a seed produced by a transgenic plant expressing a TFSRP, wherein the seed contains the TFSRP, and wherein the plant is true breeding for increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* TFSRPs, LZ-2, LZ-3, DBF-2, and DBF-3; the *Brassica napus* TFSRP, BnDBF-1; and the *Oryza sativa* TFSRPS, OsDBF-1 and OsDBF-2, are useful for increasing a plant's tolerance to environmental stress. As used herein, the term polypeptide refers to a chain of at least four amino acids joined by peptide bonds. The chain may be linear, branched, circular or combinations thereof. Accordingly, the present invention provides isolated TFSRPs selected from the group consisting of LZ-2, LZ-3, DBF-2, DBF-3, BnDBF-1, OsDBF-1; and OsDBF-2, and homologs thereof. In preferred embodiments, the TFSRP is selected from: 1) a *Physcomitrella patens* Leucine Zipper-2 (LZ-2) protein as defined in SEQ ID NO:3; 2) a *Physcomitrella patens* Leucine Zipper-3 (LZ-3) protein as defined in SEQ ID NO:6; 3) a *Physcomitrella patens* DNA-Binding Factor-2 (DBF-2) protein as defined in SEQ ID NO:9; 4) a *Physcomitrella patens* DNA-Binding Factor-3 (DBF-3) protein as defined in SEQ ID NO:12, 5) a *Brassica napus* DNA Binding Factor-1 (BnDBF-1) as defined in SEQ ID NO:14, 6) an *Oryza sativa* DNA Binding Factor-1 (OsDBF-1) as defined in SEQ ID NO:16, and 7) an *Oryza sativa* DNA Binding Factor-2 (OsDBF-2) as defined in SEQ ID NO:18, and homologs and orthologs thereof. Homologs and orthologs of the amino acid sequences are defined below.

The TFSRPs of the present invention are preferably produced by recombinant DNA techniques. For example, a nucleic acid molecule encoding the polypeptide is cloned into an expression vector (as described below), the expression vector is introduced into a host cell (as described below), and the TFSRP is expressed in the host cell. The TFSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a TFSRP polypeptide, or peptide thereof, can be synthesized chemically using standard peptide synthesis techniques. Moreover, native TFSRP can be isolated from cells (e.g., *Physcomitrella patens, Brassica napus*, or *Oryza sativa*), for example using an anti-TFSRP antibody, which can be produced by standard techniques utilizing a TFSRP or fragment thereof.

The invention further provides an isolated TFSRP coding nucleic acid. The present invention includes TFSRP coding nucleic acids that encode TFSRPs as described herein. In preferred embodiments, the TFSRP coding nucleic acid is selected from 1) a *Physcomitrella* patens Leucine Zipper-2 (LZ-2) nucleic acid as defined in SEQ ID NO:2; 2) a *Physcomitrella patens* Leucine Zipper-3 (LZ-3) nucleic acid as defined in SEQ ID NO:5; 3) a *Physcomitrella* patens DNA-Binding Factor-2 (DBF-2) nucleic acid as defined in SEQ ID NO:8; 4) a *Physcomitrella patens* DNA-Binding Factor-3 (DBF-3) nucleic acid as defined in SEQ ID NO:11, 5) a *Brassica napus* DNA Binding Factor-1 (BnDBF-1) nucleic acid as defined in SEQ ID NO:13, 6) an *Oryza sativa* DNA Binding Factor-1 (OsDBF-1) nucleic acid as defined in SEQ ID NO:15, and 7) an *Oryza sativa* DNA Binding Factor-2 (OsDBF-2) nucleic acid as defined in SEQ ID NO:17, and homologs and orthologs thereof. Homologs and orthologs of the nucleotide sequences are defined below. In one preferred embodiment, the nucleic acid and polypeptide are isolated from the plant genus *Physcomitrella, Brassica,* or *Oryza*. In another preferred embodiment, the nucleic acid and polypeptide are from a *Physcomitrella patens* (*P. patens*) plant, a *Brassica napus* plant, or an *Oryza sativa* plant.

As used herein, the term "environmental stress" refers to any sub-optimal growing condition and includes, but is not limited to, sub-optimal conditions associated with salinity, drought, temperature, metal, chemical, pathogenic, and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. Also included within the definition of "environmental stress" is lodging, or the bending of shoots or stems in response to elements such as wind, rain, pests, or disease. Accordingly, the present invention provides compositions and methods of increasing lodging resistance in a plant. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. In various embodiments, the isolated TFSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* cell, a *Brassica napus* cell, or an *Oryza sativa* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:2, SEQ ID NO:5, SEQ ID NO:8, SEQ ID NO:11, SEQ ID NO:13, SEQ ID NO:15, SEQ ID NO:17, or a portion thereof, can be isolated using standard molecular biology techniques and the sequence information provided herein. For example, a *P. patens* TFSRP cDNA can be isolated from a *P. patens* library using all or portion of one of the sequences of SEQ ID NO:1, SEQ ID NO:4, SEQ ID NO:7, and SEQ ID NO:10. Moreover, a nucleic acid molecule encompassing all or a portion of one of the sequences of SEQ ID NO:2, SEQ ID NO:5, SEQ ID NO:8, SEQ ID NO:11, SEQ ID NO:13, SEQ ID NO:15, or SEQ ID NO:17 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294–5299), and cDNA can be prepared using reverse transcriptase (e.g., Moloney MLV reverse transcriptase, available from Gibco/ BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:2, SEQ ID NO:5, SEQ ID NO:8, SEQ ID NO:11, SEQ ID NO:13, SEQ ID NO:15, and SEQ ID NO:17. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a TFSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:2, SEQ ID NO:5, SEQ ID NO:8, SEQ ID NO:11, SEQ ID NO:13, SEQ ID NO:15, or SEQ ID NO:17. These cDNAs may comprise sequences encoding the TFSRPs, (i.e., the "coding region"), as well as 5' untranslated sequences and 3' untranslated sequences. It is to be understood that SEQ ID NO:2, SEQ ID NO:5, SEQ ID NO:8, and SEQ ID NO:11 comprise both coding regions and 5' and 3' untranslated regions. Alternatively, the nucleic acid molecules of the present invention can comprise only the coding region of any of the sequences in SEQ ID NO:2, SEQ ID NO:5, SEQ ID NO:8, SEQ ID NO:11, SEQ ID NO:13, SEQ ID NO:15, or SEQ ID NO:17, or can contain whole genomic fragments isolated from genomic DNA. For the sequences as defined in SEQ ID NO:2, SEQ ID NO:5, SEQ ID NO:8, and SEQ ID NO:11, the coding regions are as follows: the LZ-2 coding region comprises nucleotides 61–1470 of SEQ ID NO:2; the LZ-3 coding region comprises nucleotides 50–1372 of SEQ ID NO:5; the DBF-2 coding region comprises nucleotides 181-1380 of SEQ ID NO:8; and the DBF-3 coding region comprises nucleotides 14–637 of SEQ ID NO:11. Accordingly, the present invention includes TFSRP nucleic acids comprising nucleotides 61–1470 of SEQ ID NO:2, nucleotides 50–1372 of SEQ ID NO:5, nucleotides 181–1380 of SEQ ID NO:8, or nucleotides 14–637 of SEQ ID NO:11. The present invention also includes TFSRP coding nucleic acids that encode TFSRPs as described herein. A preferred embodiment is a TFSRP coding nucleic acid that encodes a TFSRP selected from the group consisting of LZ-2 as defined in SEQ ID NO:3, LZ-3 as defined in SEQ ID NO:6, DBF-2 as defined in SEQ ID NO:9, DBF-3 as defined in SEQ ID NO:12, BnDBF-1 as defined in SEQ ID NO:14, OsDBF-1 as defined in SEQ ID NO:16, and OsDBF-2 as defined in SEQ ID NO:18.

Moreover, the nucleic acid molecule of the invention can comprise a portion of the coding region of one of the sequences in SEQ ID NO:2, SEQ ID NO:5, SEQ ID NO:8, SEQ ID NO:11, SEQ ID NO:13, SEQ ID NO:15, or SEQ ID NO:17, for example, a fragment which can be used as a probe or primer or a fragment encoding a biologically active portion of a TFSRP. The nucleotide sequences determined from the cloning of the TFSRP genes from *Physcomitrella patens, Brassica napus*, and *Oryza sativa* allow for the generation of probes and primers designed for use in identifying and/or cloning TFSRP homologs in other cell types and organisms, as well as TFSRP homologs from other mosses and related species. The portion of the coding region can also encode a biologically active fragment of a TFSRP.

As used herein, the term "biologically active portion of" a TFSRP is intended to include a portion, e.g., a domain/motif, of a TFSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising a TFSRP expression cassette (or expression vector) as compared to the stress tolerance of a non-transgenic control plant. Methods for quantitating stress tolerance are provided at least in Example 7 below. In a preferred embodiment, the biologically active portion of a TFSRP increases a plant's tolerance to an environmental stress.

Biologically active portions of a TFSRP include peptides comprising amino acid sequences derived from the amino acid sequence of a TFSRP, e.g., an amino acid sequence of SEQ ID NO:3, SEQ ID NO:6, SEQ ID NO:9, SEQ ID NO:12, SEQ ID NO:14, SEQ ID NO:16, or SEQ ID NO:18, or the amino acid sequence of a polypeptide identical to a TFSRP, which includes fewer amino acids than a full length TFSRP or the full length polypeptide which is identical to a TFSRP, and exhibit at least one activity of a TFSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of a TFSRP. Moreover, other biologically active portions in which other regions of the polypeptide are deleted, can be prepared by recombinant techniques and evaluated for one or more of the activities described herein. Preferably, the biologically active portions of a TFSRP include one or more selected domains/motifs or portions thereof having a biological activity such as DNA binding. DNA binding domains of the polypeptides of the present invention span the following amino acids: the LZ-2 DNA binding domain spans amino acids 280–340 of SEQ ID NO:3; the LZ-3 DNA binding domain spans amino acids 254–318 of SEQ ID NO:6; the DBF-2 DNA binding domain spans amino acids 51–121 and 253–322 of SEQ ID NO:9; and the DBF-3 DNA binding domain spans amino acids 79–198 of SEQ ID NO:12. Accordingly, the present invention includes TFSRPs comprising amino acids 280–340 of SEQ ID NO:3, amino acids 254–318 of SEQ ID NO:6, amino acids 51–121 or 253–322 of SEQ ID NO:9, and amino acids 79–198 of SEQ ID NO:12.

The invention also provides TFSRP chimeric or fusion polypeptides. As used herein, a TFSRP "chimeric polypeptide" or "fusion polypeptide" comprises a TFSRP operatively linked to a non-TFSRP. A TFSRP refers to a polypeptide having an amino acid sequence corresponding to a TFSRP, whereas a non-TFSRP refers to a polypeptide having an amino acid sequence corresponding to a polypeptide which is not substantially identical to the TFSRP, e.g., a polypeptide that is different from the TFSRP and is derived from the same or a different organism. As used herein with regard to the fusion polypeptide, the term "operatively linked" is intended to indicate that the TFSRP and the non-TFSRP are fused to each other so that both sequences fulfill the proposed function attributed to the sequence used. The non-TFSRP can be fused to the N-terminus or C-terminus of the TFSRP. For example, in one embodiment, the fusion polypeptide is a GST-TFSRP fusion polypeptide in which the TFSRP sequences are fused to the C-terminus of the GST sequences. Such fusion polypeptides can facilitate the purification of recombinant TFSRPs. In another embodiment, the fusion polypeptide is a TFSRP containing a heterologous signal sequence at its N-terminus. In certain host cells (e.g., mammalian host cells), expression and/or secretion of a TFSRP can be increased through use of a heterologous signal sequence.

Preferably, a TFSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence. See, e.g., Current Protocols in Molecular Biology, Eds. Ausubel et al. John Wiley & Sons: 1992.

Moreover, many expression vectors are commercially available that already encode a fusion moiety (e.g., a GST polypeptide). A TFSRP encoding nucleic acid can be cloned into such an expression vector such that the fusion moiety is linked in-frame to the TFSRP.

In addition to fragments and fusion polypeptides of the TFSRPs described herein, the present invention includes homologs and analogs of naturally occurring TFSRPs and TFSRP encoding nucleic acids in a plant. "Homologs" are defined herein as two nucleic acids or polypeptides that have similar, or substantially identical, nucleotide or amino acid sequences, respectively. Homologs include allelic variants, orthologs, paralogs, agonists, and antagonists of TFSRPs as defined hereafter. The term "homolog" further encompasses nucleic acid molecules that differ from one of the nucleotide sequences shown in SEQ ID NO:2, SEQ ID NO:5, SEQ ID NO:8, SEQ ID NO:11, SEQ ID NO:13, SEQ ID NO:15, and SEQ ID NO:17 (and portions thereof) due to degeneracy of the genetic code and thus encode the same TFSRP as that encoded by the nucleotide sequences shown in SEQ ID NO:2, SEQ ID NO:5, SEQ ID NO:8, SEQ ID NO:11, SEQ ID NO:13, SEQ ID NO:15, or SEQ ID NO:17. As used herein a "naturally occurring" TFSRP refers to a TFSRP amino acid sequence that occurs in nature. Preferably, a naturally occurring TFSRP comprises an amino acid sequence selected from the group consisting of SEQ ID NO:3, SEQ ID NO:6, SEQ ID NO:9, SEQ ID NO:12, SEQ ID NO:14, SEQ ID NO:16, and SEQ ID NO:18.

An agonist of the TFSRP can retain substantially the same, or a subset, of the biological activities of the TFSRP. An antagonist of the TFSRP can inhibit one or more of the activities of the naturally occurring form of the TFSRP. For example, the TFSRP antagonist can competitively bind to a downstream or upstream member of the cell membrane component metabolic cascade that includes the TFSRP, or bind to a TFSRP that mediates transport of compounds across such membranes, thereby preventing translocation from taking place.

Nucleic acid molecules corresponding to natural allelic variants and analogs, orthologs and paralogs of a TFSRP cDNA can be isolated based on their identity to the *Physcomitrella patens, Brassica napus,* or *Oryza sativa* TFSRP nucleic acids described herein using TFSRP cDNAs, or a portion thereof, as a hybridization probe according to standard hybridization techniques under stringent hybridization conditions. In an alternative embodiment, homologs of the TFSRP can be identified by screening combinatorial libraries of mutants, e.g., truncation mutants, of the TFSRP for TFSRP agonist or antagonist activity. In one embodiment, a variegated library of TFSRP variants is generated by combinatorial mutagenesis at the nucleic acid level and is encoded by a variegated gene library. A variegated library of TFSRP variants can be produced by, for example, enzymatically ligating a mixture of synthetic oligonucleotides into gene sequences such that a degenerate set of potential TFSRP sequences is expressible as individual polypeptides, or alternatively, as a set of larger fusion polypeptides (e.g., for phage display) containing the set of TFSRP sequences therein. There are a variety of methods that can be used to produce libraries of potential TFSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential TFSRP sequences. Methods for synthesizing degenerate oligonucleotides are known in the art. See, e.g., Narang, S. A., 1983, Tetrahedron 39:3; Itakura et al., 1984, Annu. Rev. Biochem. 53:323; Itakura et al., 1984, Science 198:1056; Ike et al., 1983, Nucleic Acid Res. 11:477.

In addition, libraries of fragments of the TFSRP coding regions can be used to generate a variegated population of TFSRP fragments for screening and subsequent selection of homologs of a TFSRP. In one embodiment, a library of coding sequence fragments can be generated by treating a double stranded PCR fragment of a TFSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the TFSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TFSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify TFSRP homologs (Arkin and Yourvan, 1992, PNAS 89:7811–7815; Delgrave et al., 1993, Polypeptid Engineering 6(3):327–331). In another embodiment, cell based assays can be exploited to analyze a variegated TFSRP library, using methods well known in the art. The present invention further provides a method of identifying a novel TFSRP, comprising (a) raising a specific antibody response to a TFSRP, or a fragment thereof, as described herein; (b) screening putative TFSRP material with the antibody, wherein specific binding of the antibody to the material indicates the presence of a potentially novel TFSRP; and (c) analyzing the bound material in comparison to known TFSRP, to determine its novelty.

As stated above, the present invention includes TFSRPs and homologs thereof. To determine the percent sequence identity of two amino acid sequences (e.g., one of the sequences of SEQ ID NO:3, SEQ ID NO:6, SEQ ID NO:9, SEQ ID NO:12, SEQ ID NO:14, SEQ ID NO:16, and SEQ ID NO:18 and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:3, SEQ ID NO:6, SEQ ID NO:9, SEQ ID NO:12, SEQ ID NO:14, SEQ ID NO:16, and SEQ ID NO:18) is occupied by the same amino acid residue at the corresponding position in the other sequence (e.g., a mutant form of the sequence selected from the polypeptide of SEQ ID NO:3, SEQ ID NO:6, SEQ ID NO:9, SEQ ID NO:12, SEQ ID NO:14, SEQ ID NO:16, and SEQ ID NO:18), then the molecules are identical at that position.

The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50–60%, preferably at least about 60–70%, and more preferably at least about 70–75%, 75–80%, 80–85%, 85–90% or 90–95%, and most preferably at least about 96%, 97%, 98%, 99% or more identical to an entire amino acid sequence shown in SEQ ID NO:3, SEQ ID NO:6, SEQ ID NO:9, SEQ ID NO:12, SEQ ID NO:14, SEQ ID NO:16, and SEQ ID NO:18. In yet another embodiment, the isolated amino acid homologs included in the present invention are at least about 50–60%, preferably at least about 60–70%, and more preferably at least about 70–75%, 75–80%, 80–85%, 85–90% or 90–95%, and most preferably at least about 96%, 97%, 98%, 99% or more identical to an entire amino acid sequence encoded by a nucleic acid sequence shown in SEQ ID NO:2, SEQ ID NO:5, SEQ ID NO:8, SEQ ID NO:11, SEQ ID NO:13, SEQ ID NO:15, and SEQ ID NO:17. In other embodiments, the TFSRP amino acid homologs have sequence identity over at least 15 contiguous amino acid residues, more preferably at least 25 contiguous amino acid residues, and most preferably at least 35 contiguous amino acid residues of SEQ ID NO:3, SEQ ID NO:6, SEQ ID NO:9, SEQ ID NO:12, SEQ ID NO:14, SEQ ID NO:16, or SEQ ID NO:18. In one embodiment of the present invention, the homolog has at least about 50–60%, preferably at least about 60–70%, more preferably at least about 70–75%, 75–80%, 80–85%, 85–90% or 90–95%, and even more preferably at least a 95%, 96%, 97%, 98%, 99% or more sequence identity with the DNA binding domain of LZ-2 (amino acids 280–340 of SEQ ID NO:3), LZ-3 (amino acids 254–318 of SEQ ID NO:6), DBF-2 (amino acids 51–121 or 253–322 of SEQ ID NO:9), or DBF-3 (amino acids 79–198 of SEQ ID NO:12).

In another preferred embodiment, an isolated nucleic acid homolog of the invention comprises a nucleotide sequence which is at least about 50–60%, preferably at least about 60–70%, more preferably at least about 70–75%, 75–80%, 80–85%, 85–90% or 90–95%, and even more preferably at least about 95%, 96%, 97%, 98%, 99% or more identical to a nucleotide sequence shown in SEQ ID NO:2, SEQ ID NO:5, SEQ ID NO:8, SEQ ID NO:11, SEQ ID NO:13, SEQ ID NO:15, and SEQ ID NO:17, or to a portion comprising at least 60 consecutive nucleotides thereof. The preferable length of sequence comparison for nucleic acids is at least 75 nucleotides, more preferably at least 100 nucleotides and most preferably the entire length of the coding region.

It is further preferred that the isolated nucleic acid homolog of the invention encodes a TFSRP, or portion thereof, that is at least 76% identical to an amino acid sequence of SEQ ID NO:3, SEQ ID NO:6, SEQ ID NO:9, SEQ ID NO:12, SEQ ID NO:14, SEQ ID NO:16, or SEQ ID NO:18, and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes a TFSRP that functions as a transcription factor.

For the purposes of the invention, the percent sequence identity between two nucleic acid or polypeptide sequences may be determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:2, SEQ ID NO:5, SEQ ID NO:8, SEQ ID NO:11, SEQ ID NO:13, SEQ ID NO:15, or SEQ ID NO:17 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:2, SEQ ID NO:5, SEQ ID NO:8, SEQ ID NO:11, SEQ ID NO:13, SEQ ID NO:15, or SEQ ID NO:17. In other embodiments, the nucleic acid is at least 30, 50, 100, 250 or more nucleotides in length. Preferably, an isolated nucleic acid homolog of the invention comprises a nucleotide sequence which hybridizes under highly stringent conditions to the nucleotide sequence shown in SEQ ID NO:2, SEQ ID NO:5, SEQ ID NO:8, SEQ ID NO:11, SEQ ID NO:13, SEQ ID NO:15, or SEQ ID NO:17 and functions as a modulator of stress tolerance in a plant. In a further preferred embodiment, overexpression of the isolated nucleic acid homolog in a plant increases a plant's tolerance to an environmental stress. In an even further preferred embodiment, the isolated nucleic acid homolog encodes a TFSRP that functions as a transcription factor.

As used herein with regard to hybridization for DNA to DNA blot, the term "stringent conditions" refers to hybridization overnight at 60° C. in 10× Denhart's solution, 6× SSC, 0.5% SDS and 100 µg/ml denatured salmon sperm DNA. Blots are washed sequentially at 62° C. for 30 minutes each time in 3× SSC/0.1% SDS, followed by 1× SSC/0.1% SDS and finally 0.1× SSC/0.1% SDS. As also used herein, "highly stringent conditions" refers to hybridization overnight at 65° C. in 10× Denhart's solution, 6× SSC, 0.5% SDS and 100 µg/ml denatured salmon sperm DNA. Blots are washed sequentially at 65° C. for 30 minutes each time in 3× SSC/0.1% SDS, followed by 1× SSC/0.1% SDS and finally 0.1× SSC/0.1% SDS. Methods for nucleic acid hybridizations are described in Meinkoth and Wahl, 1984, Anal. Biochem. 138:267–284; Ausubel et al. Eds., 1995, Current Protocols in Molecular Biology, Chapter 2, Greene Publishing and Wiley-Interscience, New York; and Tijssen, 1993, Laboratory Techniques in Biochemistry and Molecular Biology: Hybridization with Nucleic Acid Probes, Part I, Chapter 2, Elsevier, New York. Preferably, an isolated nucleic acid molecule of the invention that hybridizes under stringent or highly stringent conditions to a sequence of SEQ ID NO:2, SEQ ID NO:5, SEQ ID NO:8, SEQ ID NO:11, SEQ ID NO:13, SEQ ID NO:15, or SEQ ID NO:17 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens, Brassica napus,* or *Oryza sativa* TFSRP.

Using the above-described methods, and others known to those of skill in the art, one of ordinary skill in the art can isolate homologs of the TFSRPs comprising an amino acid sequence shown in SEQ ID NO:3, SEQ ID NO:6, SEQ ID NO:9, SEQ ID NO:12, SEQ ID NO:14, SEQ ID NO:16, or SEQ ID NO:18. One subset of these homologs is allelic variants. As used herein, the term "allelic variant" refers to a nucleotide sequence containing polymorphisms that lead to changes in the amino acid sequences of a TFSRP and that exist within a natural population (e.g., a plant species or variety). Such natural allelic variations can typically result in 1–5% variance in a TFSRP nucleic acid. Allelic variants can be identified by sequencing the nucleic acid sequence of interest in a number of different plants, which can be readily carried out by using hybridization probes to identify the same TFSRP genetic locus in those plants. Any and all such nucleic acid variations and resulting amino acid polymorphisms or variations in a TFSRP that are the result of natural allelic variation and that do not alter the functional activity of a TFSRP, are intended to be within the scope of the invention.

Moreover, nucleic acid molecules encoding TFSRPs from the same or other species such as TFSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338): 631–637). Analogs, orthologs and paralogs of a naturally occurring TFSRP can differ from the naturally occurring TFSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80–85%, more preferably, 85–90% or 90–95%, and most preferably 95%, 96%, 97%, 98% or even 99% identity or sequence identity with all or part of a naturally occurring TFSRP amino acid sequence and will exhibit a function similar to a TFSRP. Preferably, a TFSRP ortholog of the present invention functions as a modulator of an environmental stress response in a plant and/or functions as a transcription factor. More preferably, a TFSRP ortholog increases the stress tolerance of a plant. In one embodiment, the TFSRP orthologs maintain the ability to participate in the metabolism of compounds necessary for the construction of cellular membranes in a plant, or in the transport of molecules across these membranes.

In addition to naturally-occurring variants of a TFSRP sequence that may exist in the population, the skilled artisan will further appreciate that changes can be introduced by mutation into a nucleotide sequence of SEQ ID NO:2, SEQ ID NO:5, SEQ ID NO:8, SEQ ID NO:11, SEQ ID NO:13, SEQ ID NO:15, or SEQ ID NO:17, thereby leading to changes in the amino acid sequence of the encoded TFSRP, without altering the functional activity of the TFSRP. For example, nucleotide substitutions leading to amino acid substitutions at "non-essential" amino acid residues can be made in a sequence of SEQ ID NO:2, SEQ ID NO:5, SEQ ID NO:8, SEQ ID NO:11, SEQ ID NO:13, SEQ ID NO:15, or SEQ ID NO:17. A "non-essential" amino acid residue is a residue that can be altered from the wild-type sequence of one of the TFSRPs without altering the activity of said TFSRP, whereas an "essential" amino acid residue is required for TFSRP activity. Other amino acid residues, however, (e.g., those that are not conserved or only semi-conserved in the domain having TFSRP activity) may not be essential for activity and thus are likely to be amenable to alteration without altering TFSRP activity.

Accordingly, another aspect of the invention pertains to nucleic acid molecules encoding TFSRPs that contain changes in amino acid residues that are not essential for TFSRP activity. Such TFSRPs differ in amino acid sequence from a sequence contained in SEQ ID NO:3, SEQ ID NO:6, SEQ ID NO:9, SEQ ID NO:12, SEQ ID NO:14, SEQ ID NO:16, or SEQ ID NO:18 yet retain at least one of the TFSRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:3, SEQ ID NO:6, SEQ ID NO:9, SEQ ID NO:12, SEQ ID NO:14, SEQ ID NO:16, or SEQ ID NO:18. Preferably, the polypeptide encoded by the nucleic acid molecule is at least about 50–60% identical to one of the sequences of SEQ ID NO:3, SEQ ID NO:6, SEQ ID NO:9, SEQ ID NO:12, SEQ ID NO:14, SEQ ID NO:16, or SEQ ID NO:18, more preferably at least about 60–70% identical to one of the sequences of SEQ ID NO:3, SEQ ID NO:6, SEQ ID NO:9, SEQ ID NO:12, SEQ ID NO:14, SEQ ID NO:16, or SEQ ID NO:18, even more preferably at least about 70–75%, 75–80%, 80–85%, 85–90%, 90–95% identical to one of the sequences of SEQ ID NO:3, SEQ ID NO:6, SEQ ID NO:9, SEQ ID NO:12, SEQ ID NO:14, SEQ ID NO:16, or SEQ ID NO:18, and most preferably at least about 96%, 97%, 98%, or 99% identical to one of the sequences of SEQ ID NO:3, SEQ ID NO:6, SEQ ID NO:9, SEQ ID NO:12, SEQ ID NO:14, SEQ ID NO:16, or SEQ ID NO:18. The preferred TFSRP homologs of the present invention participate in the a stress tolerance response in a plant, or more particularly, participate in the transcription of a polypeptide involved in a stress tolerance response in a plant, and/or function as a transcription factor.

An isolated nucleic acid molecule encoding a TFSRP having sequence identity with a polypeptide sequence of SEQ ID NO:3, SEQ ID NO:6, SEQ ID NO:9, SEQ ID NO:12, SEQ ID NO:14, SEQ ID NO:16, or SEQ ID NO:18 can be created by introducing one or more nucleotide substitutions, additions or deletions into a nucleotide sequence of SEQ ID NO:2, SEQ ID NO:5, SEQ ID NO:8, SEQ ID NO:11, SEQ ID NO:13, SEQ ID NO:15, or SEQ ID NO:17, respectively, such that one or more amino acid substitutions, additions or deletions are introduced into the encoded polypeptide. Mutations can be introduced into one of the sequences of SEQ ID NO:2, SEQ ID NO:5, SEQ ID NO:8, SEQ ID NO:11, SEQ ID NO:13, SEQ ID NO:15, or SEQ ID NO:17 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a TFSRP is preferably replaced with another amino acid residue from the same side chain family. Alternatively, in another embodiment, mutations can be introduced randomly along all or part of a TFSRP coding sequence, such as by saturation mutagenesis, and the resultant mutants can be screened for a TFSRP activity described herein to identify mutants that retain TFSRP activity. Following mutagenesis of one of the sequences of SEQ ID NO:2, SEQ ID NO:5, SEQ ID NO:8, SEQ ID NO:11, SEQ ID NO:13, SEQ ID NO:15, or SEQ ID NO:17, the encoded polypeptide can be expressed recombinantly and the activity of the polypeptide can be determined by analyzing the stress tolerance of a plant expressing the polypeptide as described in Example 7.

Additionally, optimized TFSRP nucleic acids can be created. Preferably, an optimized TFSRP nucleic acid encodes a TFSRP that binds to DNA, functions as a transcription factor, and/or modulates a plant's tolerance to an environmental stress, and more preferably increases a plant's tolerance to an environmental stress upon its overexpression in the plant. As used herein, "optimized" refers to a nucleic acid that is genetically engineered to increase its expression in a given plant or animal. To provide plant optimized TFSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) to eliminate sequences that cause destabilization, inappropriate polyadenylation, degradation and termination of RNA, or that form secondary structure hairpins or RNA splice sites. Increased expression of TFSRP nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324–3328; and Murray et al., 1989, Nucleic Acids Res. 17:477–498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n=1 \ Z \ X_n - Y_n \ X_n$ times 100 Z where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a TFSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized TFSRP nucleic acids of this invention also preferably have CG and TA doublet avoidance indices closely approximating those of the chosen host plant (i.e., *Physcomitrella patens, Brassica napus*, or *Oryza sativa*). More preferably these indices deviate from that of the host by no more than about 10–15%.

In addition to the nucleic acid molecules encoding the TFSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:3, SEQ ID NO:6, SEQ ID NO:9, SEQ ID NO:12, SEQ ID NO:14, SEQ ID NO:16, or SEQ ID NO:18.

The antisense nucleic acid can be complementary to an entire TFSRP coding strand, or to only a portion thereof. In one embodiment, an antisense nucleic acid molecule is antisense to a "coding region" of the coding strand of a nucleotide sequence encoding a TFSRP. The term "coding region" refers to the region of the nucleotide sequence comprising codons that are translated into amino acid residues (e.g., the entire coding region of LZ-2 comprises nucleotides 61–1470 of SEQ ID NO:2). In another embodiment, the antisense nucleic acid molecule is antisense to a "noncoding region" of the coding strand of a nucleotide sequence encoding a TFSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of TFSRP mRNA, but more preferably is an oligonucleotide which is antisense to only a portion of the coding or noncoding region of TFSRP mRNA. For example, the antisense oligonucleotide can be complementary to the region surrounding the translation start site of TFSRP mRNA. An antisense oligonucleotide can be, for example, about 5, 10, 15, 20, 25, 30, 35, 40, 45 or 50 nucleotides in length. Typically, the antisense molecules of the present invention comprise an RNA having 60–100% sequence identity with at least 14 consecutive nucleotides of SEQ ID NO:2, SEQ ID NO:5, SEQ ID NO:8, SEQ ID NO:11, SEQ ID NO:13, SEQ ID NO:15, or SEQ ID NO:17, or a polynucleotide encoding SEQ ID NO:3, SEQ ID NO:6, SEQ ID NO:9, SEQ ID NO:12, SEQ ID NO:14, SEQ ID NO:16, or SEQ ID NO:18. Preferably, the sequence identity will be at least 70%, more preferably at least 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylguanine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625–6641). The antisense nucleic acid molecule can also comprise a 2'-o-methylribonucleotide (Inoue et al., 1987, Nucleic Acids Res. 15:6131–6148) or a chimeric RNA-DNA analogue (Inoue et al., 1987, FEBS Lett. 215: 327–330).

The antisense nucleic acid molecules of the invention are typically administered to a cell or generated in situ such that they hybridize with or bind to cellular mRNA and/or genomic DNA encoding a TFSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a TFSRP polypeptide. By "ribozyme" is meant a catalytic RNA-based enzyme with ribonuclease activity which is capable of cleaving a single-stranded nucleic acid, such as an mRNA, to which it has a complementary region. Ribozymes (e.g., hammerhead ribozymes described in Haselhoff and Gerlach, 1988, Nature 334:585–591) can be used to catalytically cleave TFSRP mRNA transcripts to thereby inhibit translation of TFSRP mRNA. A ribozyme having specificity for a TFSRP-encoding nucleic acid can be designed based upon the nucleotide sequence of a TFSRP cDNA, as disclosed herein (i.e., SEQ ID NO:2, SEQ ID NO:5, SEQ ID NO:8, SEQ ID NO:11, SEQ ID NO:13, SEQ ID NO:15, or SEQ ID NO:17) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a TFSRP-encoding mRNA. See, e.g., U.S. Pat. Nos. 4,987, 071 and 5,116,742 to Cech et al. Alternatively, TFSRP mRNA can be used to select a catalytic RNA having a specific ribonuclease activity from a pool of RNA molecules. See, e.g., Bartel, D. and Szostak, J. W., 1993, Science 261:1411–1418. In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:3, SEQ ID NO:6, SEQ ID NO:9, SEQ ID NO:12, SEQ ID NO:14, SEQ ID NO:16, or SEQ ID NO:18, or a polypeptide having at least 76% sequence identity with SEQ ID NO:3, SEQ ID NO:6, SEQ ID NO:9, SEQ ID NO:12, SEQ ID NO:14, SEQ ID NO:16, or SEQ ID NO:18. The hybridizing RNAs may be substantially or completely complementary. As used herein, the phrase "substantially complementary" refers to hybridizing RNAs wherein the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides or ribonucleotide analogs, such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, for example, U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645–650 and Cooney et al., 1988, Science 241:456–459) and co-suppression (Napoli et al., 1990, The Plant Cell 2:279–289) are known in the art. Partial and full-length cDNAs have been used for the co-suppression of endogenous plant genes. See, e.g., U.S. Pat. Nos. 4,801,340, 5,034,323, 5,231,020 and 5,283,184; Van der Kroll et al., 1990, The Plant Cell 2:291–299, Smith et al., 1990, Mol. Gen. Genetics 224:477–481; and Napoli et al., 1990, The Plant Cell 2:279–289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of SEQ ID NO:2, SEQ ID NO:5, SEQ ID NO:8, SEQ ID NO:11, SEQ ID NO:13, SEQ ID NO:15, or SEQ ID NO:17. The regions of identity can comprise introns and and/or exons and untranslated regions. The introduced sense polynucleotide may be present in the plant cell transiently, or may be stably integrated into a plant chromosome or extrachromosomal replicon.

Alternatively, TFSRP gene expression can be inhibited by targeting nucleotide sequences complementary to the regulatory region of a TFSRP nucleotide sequence (e.g., a TFSRP promoter and/or enhancer) to form triple helical structures that prevent transcription of a TFSRP gene in target cells. See generally, Helene, C., 1991, Anticancer Drug Des. 6(6):569–84; Helene, C. et al., 1992, Ann. N.Y. Acad. Sci. 660:27–36; and Maher, L. J., 1992, Bioassays 14(12):807–15.

In addition to the TFSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:2, SEQ ID NO:5, SEQ ID NO:8, SEQ ID NO:11, SEQ ID NO:13, SEQ ID NO:15, or SEQ ID NO:17, an anti-sense sequence of one of the sequences set forth in SEQ ID NO:2, SEQ ID NO:5, SEQ ID NO:8, SEQ ID NO:11, SEQ ID NO:13, SEQ ID NO:15, or SEQ ID NO:17, or naturally occurring mutants thereof. Primers based on a nucleotide sequence of SEQ ID NO:2, SEQ ID NO:5, SEQ ID NO:8, SEQ ID NO:11, SEQ ID NO:13, SEQ ID NO:15, or SEQ ID NO:17 can be used in PCR reactions to clone TFSRP homologs. Probes based on the TFSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a TFSRP, such as by measuring a level of a TFSRP-encoding nucleic acid, in a sample of cells, e.g., detecting TFSRP mRNA levels or determining whether a genomic TFSRP gene has been mutated or deleted.

In particular, a useful method to ascertain the level of transcription of the gene (an indicator of the amount of mRNA available for translation to the gene product) is to perform a Northern blot. For reference, see, for example, Ausubel et al., 1988, Current Protocols in Molecular Biology, Wiley: New York. The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317–326. To assess the presence or relative quantity of polypeptide translated from this mRNA, standard techniques, such as a Western blot, may be employed. These techniques are well known to one of ordinary skill in the art. See, for example, Ausubel et al., 1988, Current Protocols in Molecular Biology, Wiley: New York.

The invention further provides an isolated recombinant expression vector comprising a TFSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990); and Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., TFSRPs, mutant forms of TFSRPs, fusion polypeptides, etc.).

The recombinant expression vectors of the invention can be designed for expression of TFSRPs in prokaryotic or eukaryotic cells. For example, TFSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423–488; van den Hondel, C. A. M. J. J. et al., 1991, Heterologous gene expression in filamentous fungi, in: More Gene Manipulations in Fungi, J. W. Bennet & L. L. Lasure, eds., p. 396–428: Academic Press: San Diego; and van den Hondel, C. A. M. J. J. & Punt, P. J., 1991, Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999, Marine Biotechnology 1(3):239–251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583–586; Plant Molecular Biology and Biotechnology, C Press, Boca Raton, Fla., chapter 6/7, S.71–119 (1993); F. F. White, B. Jenes et al., Techniques for Gene Transfer, in: Transgenic Plants, Vol. 1, Engineering and Utilization, eds. Kung and R. Wu, 128–43, Academic Press: 1993; Potrykus, 1991 Annu. Rev. Plant Physiol. Plant Molec. Biol. 42:205–225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31–40), pMAL (New England Biolabs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the TFSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant TFSRP unfused to GST can be recovered by cleavage of the fusion polypeptide with thrombin.

Examples of suitable inducible non-fusion *E. coli* expression vectors include pTrc (Amann et al., 1988, Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology: Methods in Enzymology 185, Academic Press, San Diego, Calif. (1990) 119–128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111–2118). Such alteration of nucleic acid sequences of the invention can be carried out by standard DNA synthesis techniques.

In another embodiment, the TFSRP expression vector is a yeast expression vector. Examples of vectors for expression in yeast *S. cerevisiae* include pYepSec1 (Baldari et al., 1987, EMBO J. 6:229–234), pMFa (Kujan and Herskowitz, 1982, Cell 30:933–943), pJRY88 (Schultz et al., 1987, Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, "Gene transfer systems and vector development for filamentous fungi," in: Applied Molecular Genetics of Fungi, J. F. Peberdy, et al., eds., p. 1–28, Cambridge University Press: Cambridge.

Alternatively, the TFSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell Biol. 3:2156–2165) and the pVL series (Lucklow and Summers, 1989, Virology 170:31–39).

In yet another embodiment, a TFSRP nucleic acid of the invention is expressed in mammalian cells using a mammalian expression vector. Examples of mammalian expression vectors include pCDM8 (Seed B., 1987, Nature 329:840) and pMT2PC (Kaufman et al., 1987, EMBO J. 6:187–195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. $2^{nd}$, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268–277), lymphoid-specific promoters (Calame and Eaton, 1988, Adv. Immunol. 43:235–275), in particular promoters of T cell receptors (Winoto and Baltimore, 1989, EMBO J. 8:729–733) and immunoglobulins (Banerji et al., 1983, Cell 33:729–740; Queen and Baltimore, 1983, Cell 33:741–748), neuron-specific promoters (e.g., the neurofilament promoter; Byrne and Ruddle, 1989, PNAS 86:5473–5477), pancreas-specific promoters (Edlund et al., 1985, Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, Science 249:374–379) and the fetopolypeptide promoter (Campes and Tilghman, 1989, Genes Dev. 3:537–546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, and methotrexate, or in plants that confer resistance towards a herbicide such as glyphosate or glufosinate. Nucleic acid molecules encoding a selectable marker can be introduced into a host cell on the same vector as that encoding a TFSRP or can be introduced on a separate vector. Cells stably transfected with the introduced nucleic acid molecule can be identified by, for example, drug selection (e.g., cells that have incorporated the selectable marker gene will survive, while the other cells die).

In a preferred embodiment of the present invention, the TFSRPs are expressed in plants and plants cells such as unicellular plant cells (e.g. algae) (See Falciatore et al., 1999, Marine Biotechnology 1(3):239–251 and references therein) and plant cells from higher plants (e.g., the spermatophytes, such as crop plants). A TFSRP may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contain the TFSRP nucleic acid, followed by breeding of the transformed gametes.

Other suitable methods for transforming or transfecting host cells including plant cells can be found in Sambrook, et al., Molecular Cloning: A Laboratory Manual. $2^{nd}$, ed., Cold Spring Harbor Laboratory, Cold Spring Harbor Laboratory Press, Cold Spring Harbor, N.Y., 1989, and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a TFSRP into a plant is achieved by *Agrobacterium* mediated gene transfer. *Agrobacterium* mediated plant transformation can be performed using, for example, the GV3101 (pMP90) (Koncz and Schell, 1986, Mol. Gen. Genet. 204: 383–396) or LBA4404 (Clontech) *Agrobacterium tumefaciens* strain. Transformation can be performed by standard transformation and regeneration techniques (Deblaere et al., 1994, Nucl. Acids. Res. 13:4777–4788; Gelvin, Stanton B. and Schilperoort, Robert A, Plant Molecular Biology Manual, 2$^{nd}$ Ed.—Dordrecht:Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238–242; De Block et al., 1989, Plant Physiol. 91:694–701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282–285. Additionally, transformation of soybean can be performed using, for example, a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced TFSRP may be maintained in the plant cell stably if it is incorporated into a non-chromosomal autonomous replicon or integrated into the plant chromosomes. Alternatively, the introduced TFSRP may be present on an extra-chromosomal non-replicating vector and be transiently expressed or transiently active.

In one embodiment, a homologous recombinant microorganism can be created wherein the TFSRP is integrated into a chromosome, a vector is prepared which contains at least a portion of a TFSRP gene into which a deletion, addition, or substitution has been introduced to thereby alter, e.g., functionally disrupt, the TFSRP gene. Preferably, the TFSRP gene is a *Physcomitrella patens, Brassica napus*, or an *Oryza sativa* TFSRP gene, but it can be a homolog from a related plant or even from a mammalian, yeast, or insect source. In one embodiment, the vector is designed such that, upon homologous recombination, the endogenous TFSRP gene is functionally disrupted (i.e., no longer encodes a functional polypeptide; also referred to as a knock-out vector). Alternatively, the vector can be designed such that, upon homologous recombination, the endogenous TFSRP gene is mutated or otherwise altered but still encodes a functional polypeptide (e.g., the upstream regulatory region can be altered to thereby alter the expression of the endogenous TFSRP). To create a point mutation via homologous recombination, DNA-RNA hybrids can be used in a technique known as chimeraplasty (Cole-Strauss et al., 1999, Nucleic Acids Research 27(5):1323–1330 and Kmiec, 1999, Gene therapy American Scientist 87(3):240–247). Homologous recombination procedures in *Physcomitrella patens* are also well known in the art and are contemplated for use herein.

Whereas in the homologous recombination vector, the altered portion of the TFSRP gene is flanked at its 5' and 3' ends by an additional nucleic acid molecule of the TFSRP gene to allow for homologous recombination to occur between the exogenous TFSRP gene carried by the vector and an endogenous TFSRP gene, in a microorganism or plant. The additional flanking TFSRP nucleic acid molecule is of sufficient length for successful homologous recombination with the endogenous gene. Typically, several hundreds of base pairs up to kilobases of flanking DNA (both at the 5' and 3' ends) are included in the vector. See e.g., Thomas, K. R., and Capecchi, M. R., 1987, Cell 51:503 for a description of homologous recombination vectors or Strepp et al., 1998, PNAS, 95 (8):4368–4373 for cDNA based recombination in *Physcomitrella patens*. The vector is introduced into a microorganism or plant cell (e.g., via polyethylene glycol mediated DNA), and cells in which the introduced TFSRP gene has homologously recombined with the endogenous TFSRP gene are selected using art-known techniques.

In another embodiment, recombinant microorganisms can be produced that contain selected systems which allow for regulated expression of the introduced gene. For example, inclusion of a TFSRP gene on a vector placing it under control of the lac operon permits expression of the TFSRP gene only in the presence of IPTG. Such regulatory systems are well known in the art.

Whether present in an extra-chromosomal non-replicating vector or a vector that is integrated into a chromosome, the TFSRP polynucleotide preferably resides in a plant expression cassette. A plant expression cassette preferably contains regulatory sequences capable of driving gene expression in plant cells that are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693–8711). Examples of plant expression vectors include those detailed in: Becker, D. et al., 1992, New plant binary vectors with selectable markers located proximal to the left border, Plant Mol. Biol. 20:1195–1197; Bevan, M. W., 1984, Binary *Agrobacterium* vectors for plant transformation, Nucl. Acid. Res. 12:8711–8721; and Vectors for Gene Transfer in Higher Plants; in: Transgenic Plants, Vol. 1, Engineering and Utilization, eds.: Kung and R. Wu, Academic Press, 1993, S. 15–38.

Plant gene expression should be operatively linked to an appropriate promoter conferring gene expression in a timely, cell or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and Rhizobium.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810–812), the sX CaMV $^{35}$S promoter (Kay et al., 1987, Science 236:1299–1302) the Sep1 promoter, the rice actin promoter (McElroy et al., 1990, Plant Cell 2:163–171), the *Arabidopsis* actin promoter, the ubiquitan promoter (Christensen et al., 1989, Plant Molec. Biol. 18:675–689); pEmu (Last et al., 1991, Theor Appl Genet 81:581–588), the figwort mosaic virus 35S promoter, the Smas promoter (Velten et al., 1984, EMBO J 3:2723–2730), the GRP1–8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, Arabidopsis, and maize are inducible by infection with a pathogen; and the Adh1 promoter is induced by hypoxia and cold stress. Plant gene expression can also be facilitated via an inducible promoter (For a review, see Gatz, 1997, Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397–404), and an ethanol inducible promoter (PCT Application No. WO 93/21334).

In one preferred embodiment of the present invention, the inducible promoter is a stress-inducible promoter. Stress inducible promoters include, but are not limited to, Cor78 (Chak et al., 2000, Planta 210:875–883; Hovath et al., 1993, Plant Physiol. 103:1047–1053), Cor15a (Artus et al., 1996, PNAS 93(23):13404–09), Rci2A (Medina et al., 2001, Plant Physiol. 125:1655–66; Nylander et al., 2001, Plant Mol. Biol. 45:341–52; Navarre and Goffeau, 2000, EMBO J. 19:2515–24; Capel et al., 1997, Plant Physiol. 115:569–76), Rd22 (Xiong et al., 2001, Plant Cell 13:2063–83; Abe et al., 1997, Plant Cell 9:1859–68; Iwasaki et al., 1995, Mol. Gen. Genet. 247:391–8), cDet6 (Lang and Palve, 1992, Plant Mol. Biol. 20:951–62), ADH1 (Hoeren et al., 1998, Genetics 149:479–90), KAT1 (Nakamura et al., 1995, Plant Physiol. 109:371–4), KST1 (Müller-Röber et al., 1995, EMBO 14:2409–16) Rha1 (Terryn et al., 1993, Plant Cell 5:1761–9; Terryn et al., 1992, FEBS Lett. 299(3):287–90), ARSK1 (Atkinson et al., 1997, GenBank Accession # L22302 and PCT Application No. WO 97/20057), PtxA (Plesch et al., GenBank Accession # X67427), SbHRGP3 (Ahn et al., 1996, Plant Cell 8:1477–90), GH3 (Liu et al., 1994, Plant Cell 6:645–57), the pathogen inducible PRP1-gene promoter (Ward et al., 1993, Plant. Mol. Biol. 22:361–366), the heat inducible hsp80-promoter from tomato (U.S. Pat. No. 5,187, 267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331–340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to, fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (ce1A), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from Vicia faba (Baeumlein et al., 1991, Mol Gen Genet. 225(3):459–67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233–9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086, 169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729–736).

The invention further provides a recombinant expression vector comprising a TFSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a TFSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1); and Mol et al., 1990, FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a TFSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) a TFSRP. Accordingly, the invention further provides methods for producing TFSRPs using the host cells of the invention. In one embodiment, the method comprises culturing the host cell of invention (into which a recombinant expression vector encoding a TFSRP has been introduced, or into which genome has been introduced a gene encoding a wild-type or altered TFSRP) in a suitable medium until TFSRP is produced. In another embodiment, the method further comprises isolating TFSRPs from the medium or the host cell.

Another aspect of the invention pertains to isolated TFSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of TFSRP in which the polypeptide is separated from some of the cellular components of the cells in which it is naturally or recombinantly produced. In one embodiment, the language "substantially free of cellular material" includes preparations of a TFSRP having less than about 30% (by dry weight) of non-TFSRP material (also referred to herein as a "contaminating polypeptide"), more preferably less than about 20% of non-TFSRP material, still more preferably less than about 10% of non-TFSRP material, and most preferably less than about 5% non-TFSRP material.

When the TFSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of TFSRP in which the polypeptide is separated from chemical precursors or other chemicals that are involved in the synthesis of the polypeptide. In one embodiment, the language "substantially free of chemical precursors or other chemicals" includes preparations of a TFSRP having less than about 30% (by dry weight) of chemical precursors or non-TFSRP chemicals, more preferably less than about 20% chemical precursors or non-TFSRP chemicals, still more preferably less than about 10% chemical precursors or non-TFSRP chemicals, and most preferably less than about 5% chemical precursors or non-TFSRP chemicals. In preferred embodiments, isolated polypeptides, or biologically active portions thereof, lack contaminating polypeptides from the same organism from which the TFSRP is derived. Typically, such polypeptides are produced by recombinant expression of, for example, a *Physcomitrella patens, Brassica napus,* or *Oryza sativa* TFSRP in plants other than *Physcomitrella patens, Brassica napus,* or *Oryza sativa*, or microorganisms such as *C. glutamicum,* ciliates, algae or fungi.

The nucleic acid molecules, polypeptides, polypeptide homologs, fusion polypeptides, primers, vectors, and host cells described herein can be used in one or more of the following methods: identification of *Physcomitrella patens, Brassica napus,* or *Oryza sativa* and related organisms; mapping of genomes of organisms related to *Physcomitrella patens, Brassica napus,* or *Oryza sativa*; identification and localization of *Physcomitrella patens, Brassica napus,* or *Oryza sativa* sequences of interest; evolutionary studies; determination of TFSRP regions required for function; modulation of a TFSRP activity; modulation of the metabolism of one or more cell functions; modulation of the transmembrane transport of one or more compounds; modulation of stress resistance; and modulation of expression of PKSRP nucleic acids.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The TFSRP nucleic acid molecules of the invention have a variety of uses. Most importantly, the nucleic acid and amino acid sequences of the present invention can be used to transform plants, thereby inducing tolerance to stresses such as drought, high salinity, cold, or lodging. The present invention therefore provides a transgenic plant transformed by a TFSRP nucleic acid, wherein expression of the nucleic acid sequence in the plant results in increased tolerance to environmental stress or increased resistance to lodging as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass, and forage crops, for example.

In particular, the present invention describes using the expression of LZ-2, LZ-3, DBF-2 and DBF-3 of *Physcomitrella patens*; BnDBF-1 of *Brassica napus*; and OsDBF-1 and OsDBF-2 of *Oryza sativa* to engineer drought-tolerant, salt-tolerant, cold-tolerant, and/or lodging-resistant plants.

This strategy has herein been demonstrated for *Arabidopsis thaliana*, Rapeseed/Canola, soybeans, corn, and wheat, but its application is not restricted to these plants. Accordingly, the invention provides a transgenic plant containing a TFSRP such as LZ-2 as defined in SEQ ID NO:3, LZ-3 as defined in SEQ ID NO:6, DBF-2 as defined in SEQ ID NO:9, DBF-3 as defined in SEQ ID NO:12, BnDBF-1 as defined in SEQ ID NO:14, OsDBF-1 as defined in SEQ ID NO:16, and OsDBF-2 as defined in SEQ ID NO:18, wherein the plant has an increased tolerance to an environmental stress selected from drought, increased salt, decreased or increased temperature, or lodging. In preferred embodiments, the environmental stress is drought or decreased temperature.

Accordingly, the invention provides a method of producing a transgenic plant with a TFSRP coding nucleic acid, wherein expression of the nucleic acid(s) in the plant results in increased tolerance to environmental stress as compared to a wild type variety of the plant comprising: (a) introducing into a plant cell an expression vector comprising a TFSRP nucleic acid, and (b) generating from the plant cell a transgenic plant with a increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the TFSRP nucleic acid encodes a protein comprising SEQ ID NO:3, SEQ ID NO:6, SEQ ID NO:9, SEQ ID NO:12, SEQ ID NO:14, SEQ ID NO:16, or SEQ ID NO:18.

The present invention also provides a method of modulating a plant's tolerance to an environmental stress comprising, modifying the expression of a TFSRP coding nucleic acid in the plant. The plant's tolerance to the environmental stress can be increased or decreased as achieved by increasing or decreasing the expression of a TFSRP. Preferably, the plant's tolerance to the environmental stress is increased by increasing expression of a TFSRP. Expression of a TFSRP can be modified by any method known to those of skill in the art. The methods of increasing expression of TFSRPs can be used wherein the plant is either transgenic or not transgenic. In cases when the plant is transgenic, the plant can be transformed with a vector containing any of the above described TFSRP coding nucleic acids, or the plant can be transformed with a promoter that directs expression of native TFSRP in the plant, for example. The invention provides that such a promoter can be tissue specific, developmentally regulated, or stress-inducible. Alternatively, non-transgenic plants can have native TFSRP expression modified by inducing a native promoter. The expression of LZ-2 as defined in SEQ ID NO:2, LZ-3 as defined in SEQ ID NO:5, DBF-2 as defined in SEQ ID NO:8, DBF-3 as defined in SEQ ID NO:11, BnDBF-1 as defined in SEQ ID NO:13, OsDBF-1 as defined in SEQ ID NO:15, or OsDBF-2 as defined in SEQ ID NO:17 in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997, Science 275:657).

In a preferred embodiment, transcription of the TFSRP is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as a TFSRP nucleic acid. Therefore, activating and repressing ZFPs can be created that specifically recognize the TFSRP promoters described above and used to increase or decrease TFSRP expression in a plant, thereby modulating the stress tolerance of the plant. The present invention also includes identification of the homologs of LZ-2 as defined in SEQ ID NO:2, LZ-3 as defined in SEQ ID NO:5, DBF-2 as defined in SEQ ID NO:8, DBF-3 as defined in SEQ ID NO:11, BnDBF-1 as defined in SEQ ID NO:13, OsDBF-1 as defined in SEQ ID NO:15, or OsDBF-2 as defined in SEQ ID NO:17 in a target plant as well as the homolog's promoter. The invention also provides a method of increasing expression of a gene of interest within a host cell as compared to a wild type variety of the host cell, wherein the gene of interest is transcribed in response to a TFSRP, comprising: (a) transforming the host cell with an expression vector comprising a TFSRP coding nucleic acid, and (b) expressing the TFSRP within the host cell, thereby increasing the expression of the gene transcribed in response to the TFSRP, as compared to a wild type variety of the host cell.

In addition to introducing the TFSRP nucleic acid sequences into transgenic plants, these sequences can also be used to identify an organism as being *Physcomitrella patens, Brassica napus, Oryza sativa*, or a close relative thereof. Also, they may be used to identify the presence of *Physcomitrella patens, Brassica napus, Oryza sativa*, or a relative thereof in a mixed population of microorganisms. The invention provides the nucleic acid sequences of a number of *Physcomitrella patens, Brassica napus*, and *Oryza sativa* genes. By probing the extracted genomic DNA of a culture of a unique or mixed population of microorganisms under stringent conditions with a probe spanning a region of a gene which is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens, Brassica napus*, or *Oryza sativa* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The TFSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the TFSRP nucleic acid molecules of the invention may result in the production of TFSRPs having functional differences from the wild-type TFSRPs. These polypeptides may be improved in efficiency or activity, may be present in greater numbers in the cell than is usual, or may be decreased in efficiency or activity.

There are a number of mechanisms by which the alteration of a TFSRP of the invention may directly affect stress response and/or stress tolerance. In the case of plants expressing TFSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, C. glutamicum, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993, Biotechnology, vol. 3, Chapter III: Product recovery and purification, page 469–714, VCH: Weinheim; Belter, P. A. et al., 1988, Bioseparations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1–27, VCH: Weinheim; and Dechow, F. J., 1989, Separation and purification techniques in biotechnology, Noyes Publications.

For example, yeast expression vectors comprising the nucleic acids disclosed herein, or fragments thereof, can be constructed and transformed into Saccharomyces cerevisiae using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as Arabidopsis, soy, rape, maize, wheat, Medicago truncatula, etc., using standard protocols. The resulting transgenic cells and/or plants derived therefrom can then be assayed for fail or alteration of their tolerance to drought, salt, temperature, and lodging.

The engineering of one or more TFSRP genes of the invention may also result in TFSRPs having altered activities which indirectly impact the stress response and/or stress tolerance of algae, plants, ciliates or fingi or other microorganisms like C. glutamicum. For example, the normal biochemical processes of metabolism result in the production of a variety of products (e.g., hydrogen peroxide and other reactive oxygen species) which may actively interfere with these same metabolic processes. For example, peroxynitrite is known to nitrate tyrosine side chains, thereby inactivating some enzymes having tyrosine in the active site (Groves, J. T., 1999 Curr. Opin. Chem. Biol. 3(2):226–235). While these products are typically excreted, cells can be genetically altered to transport more products than is typical for a wild-type cell. By optimizing the activity of one or more TFSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17:246–252.

The aforementioned mutagenesis strategies for TFSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like C. glutamicum expressing mutated TFSRP nucleic acid and polypeptide molecules such that the stress tolerance is improved.

The present invention also provides antibodies that specifically bind to a TFSRP, or a portion thereof, as encoded by a nucleic acid described herein. Antibodies can be made by many well-known methods. See, e.g. Harlow and Lane, "Antibodies; A Laboratory Manual" Cold Spring Harbor Laboratory, Cold Spring Harbor, N.Y., (1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., 1992, Bio/Technology 10:163–167; Bebbington et al., 1992, Bio/Technology 10:169–175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual," (Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–46). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol $s^{-1}$ $m^{-2}$ (white light; Philips TL 65 W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly(A)+ RNA were isolated. The total RNA was obtained from wild-type 9 day old protonemata following the GTC-method (Reski et al., 1994, Mol. Gen. Genet., 244:352–359). The poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with protein kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands), using the material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'     SEQ ID NO:19

5'-CTAAAGGGAACAAAAGCTG-3'    SEQ ID NO:20

5'-TGTAAAACGACGGCCAGT-3'     SEQ ID NO:21
```

Sequences were processed and annotated using the software package EST-MAX commercially provided by Bio-Max (Munich, Germany). The program incorporates practically all bioinformatics methods important for functional and structural characterization of polypeptide sequences. The most important algorithms incorporated in EST-MAX are: FASTA (Very sensitive sequence database searches with estimates of statistical significance; Pearson W. R., 1990, Rapid and sensitive sequence comparison with FASTP and FASTA, Methods Enzymol. 183:63–98); BLAST (Very sensitive sequence database searches with estimates of statistical significance; Altschul S. F. et al., Basic local alignment search tool, Journal of Molecular Biology 215:403–10); PREDATOR (High-accuracy secondary structure prediction from single and multiple sequences, Frishman, D. and Argos, P., 1997, 75% accuracy in polypeptide secondary structure prediction, Polypeptides, 27:329–335); CLUSTALW (Multiple sequence alignment; Thompson, J. D. et al., 1994, CLUSTAL W: improving the sensitivity of progressive multiple sequence alignment through sequence weighting, positions-specific gap penalties and weight matrix choice. Nucleic Acids Research, 22:4673–4680); TMAP (Transmembrane region prediction from multiply aligned sequences; Persson, B. and Argos, P., 1994, Prediction of transmembrane segments in polypeptides utilizing multiple sequence alignments, J. Mol. Biol. 237:182–192); ALOM2 (Transmembrane region prediction from single sequences; Klein, P. et al., Prediction of polypeptide function from sequence properties: A discriminate analysis of a database. Biochim. Biophys. Acta 787:221–226 (1984). Version 2 by Dr. K. Nakai); PROSEARCH (Detection of PROSITE polypeptide sequence patterns; Kolakowski L. F. Jr. et al., 1992, ProSearch: fast searching of polypeptide sequences with regular expression patterns related to polypeptide structure and function, Biotechniques 13:919–921); BLIMPS (Similarity searches against a database of ungapped blocks; J. C. Wallace and Henikoff S., 1992); and PATMAT (A searching and extraction program for sequence, pattern and block queries and databases, CABIOS 8:249–254. Written by Bill Alford.).

Example 5

Identification of *Physcomitrella patens* ORFs Corresponding to LZ-2, LZ-3, DBF-2, and DBF-3

The *Physcomitrella patens* partial cDNAs (ESTs) corresponding to PpLZ-2 (SEQ ID NO:1), PpLZ-3 (SEQ ID NO:4), PpDBF-2 (SEQ ID NO:7), and PpDBF-3 (SEQ ID NO:10) were identified in the *Physcomitrella patens* EST sequencing program using the program EST-MAX through BLAST analysis as shown in Tables 1–4.

TABLE 1

Degree of amino acid identity and similarity of PpLZ-2 and other homologous proteins (Pairwise comparison program was used: gap penalty: 10; gap extension penalty: 0.1; score matrix: blosum62)

| Swiss-Prot # | Q99090 | P93839 | P93405 | Q03462 | Q9LKT9 |
|---|---|---|---|---|---|
| Protein name | Light-Inducible Protein CPRF-2 | G/HBF-1 | BZIP Protein | Opaque2 Hetero-dimerizing Protein 1 (OHP1) | Hypothetical Protein T32B20.C. |
| Species | *Petroselinum crispum* (Parsley) (*Petroselinum hortense*) | *Glycine max* (Soybean) | *Oryza sativa* (Rice) | *Zea mays* (Maize) | *Arabidopsis thaliana* (Mouse-ear cress) |
| Identity % | 29% | 28% | 27% | 27% | 28% |
| Similarity % | 38% | 34% | 36% | 34% | 36% |

TABLE 2

Degree of amino acid identity and similarity of PpLZ-3 and other homologous proteins (Pairwise comparison program was used: gap penalty: 10; gap extension penalty: 0.1; score matrix: blosum62)

| Swiss-Prot # | P93839 | Q99090 | Q03462 | Q41757 | Q41786 |
|---|---|---|---|---|---|
| Protein name | G/HBF-1 | Light-Inducible Protein CPRF-2 | Opaque2 Hetero-dimerizing Protein 1 | Opaque-2 Hetero-dimerizing Protein 1B | Opaque2 Hetero-dimerizing Protein 2 |
| Species | *Glycine max* (Soybean) | *Petroselinum crispum* (Parsley) | *Zea mays* (Maize) | *Zea mays* (Maize) | *Zea mays* (Maize) |
| Identity % | 35% | 31% | 28% | 27% | 30% |
| Similarity % | 45% | 39% | 38% | 37% | 40% |

TABLE 3

Degree of amino acid identity and similarity of PpDBF-2 and other homologous proteins (Pairwise comparison program was used: gap penalty: 10; gap extension penalty: 0.1; score matrix: blosum62)

| Swiss-Prot # | O22523 | Q96327 | Q9LKG4 | P50580 | Q9UQ80 |
|---|---|---|---|---|---|
| Protein name | DNA-Binding Protein GBP16 | Putative Nuclear DNA-Binding Protein G2P (ATG2) | Putative DNA Binding Protein | Proliferation-Associated Protein 1 | Cell Cycle Protein |
| Species | Oryza sativa (Rice) | Arabidopsis thaliana (Mouse-ear cress) | Atriplex hortensis (Mountain spinach) | Mus musculus (Mouse) | Homo sapiens (Human) |
| Identity % | 75% | 74% | 74% | 46% | 46% |
| Similarity % | 84% | 82% | 84% | 59% | 59% |

TABLE 4

Degree of amino acid identity and similarity of PpDBF-3 and other homologous proteins (Pairwise comparison program was used: gap penalty: 10; gap extension penalty: 0.1; score matrix: blosum62)

| Swiss-Prot # | O26807 | Q9KQK0 | Q9KSM0 | Q9VGV4 | Q9RUK6 |
|---|---|---|---|---|---|
| Protein name | Transcriptional Regulator | PILB-Related Protein | PILB-Related Protein | CG6584 Protein | MSRA-Related Protein |
| Species | Methanobacterium thermoautotrophicum | Vibrio cholerac | Vibrio cholerac | Droso-phila melanogaster (Fruit fly) | Deinococcus radiodurans |
| Identity % | 45% | 38% | 40% | 36% | 34% |
| Similarity % | 53% | 49% | 47% | 44% | 42% |

Example 6

Cloning of the Full-length cDNA Encoding for LZ-2, LZ-3, DBF-2, DBF-3, BnDBF-1, OsDBF-1, and OsDBF-2

Full-length clones corresponding to PpDBF-2 (SEQ ID NO:8) and PpDBF-3 (SEQ ID NO:11) were obtained by performing polymerase chain reaction (PCR) with gene-specific primers (See Table 5) and the original EST as the template since they were full-length. The conditions for the reaction are described below under "Full-length Amplification."

To isolate the full-length clones encoding for PpLZ-2 (SEQ ID NO:2), and PpLZ-3 (SEQ ID NO:5) from *Physcomitrella patens*, cDNA libraries were created with SMART RACE cDNA Amplification kit (Clontech Laboratories) following the manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points above. RNA was then pulled and used for isolation.

5' RACE Protocol

The EST sequences of PpLZ-2 (SEQ ID NO:1) and PpLZ-3 (SEQ ID NO:4) identified from the database search as described in Example 5 were used to design oligos for RACE (See Table 5). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions.

The sequences obtained from the RACE reactions contained the 5' end of the full-length coding regions of for PpLZ-2, and PpLZ-3 and were used to design oligos for full-length cloning of the respective genes (See below under "Full-length Amplification).

Full-length Amplification

Full-length clones corresponding to PpDBF-2 (SEQ ID NO:8) and PpDBF-3 (SEQ ID NO:11) were obtained by performing polymerase chain reaction (PCR) with gene-specific primers (See Table 5) and the original EST as the template. The conditions for the reaction were standard conditions with PWO DNA polymerase (Roche). PCR was performed according to standard conditions and the manufacturer's protocols (Sambrook et al., 1989, Molecular Cloning, A Laboratory Manual, 2nd Edition, Cold Spring Harbor Laboratory Press, Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty-five cycles of one minute at 94° C., one minute at 65° C., and 1.5 minutes at 72° C.

Full-length clones for PpLZ-2 (SEQ ID NO:2), and PpLZ-3 (SEQ ID NO:5) were isolated by repeating the RACE method but using the gene-specific primers as given in Table 5.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989, Molecular Cloning, A Laboratory Manual, 2nd Edition, Cold Spring Harbor Laboratory Press, Cold Spring Harbor, N.Y.). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989, Molecular Cloning, A Laboratory Manual, 2nd Edition, Cold Spring Harbor Laboratory Press. Cold Spring Harbor, N.Y.).

TABLE 5

| Gene | Sites in the final product | Isolation Method | Primers Race | Primer RT-PCR |
|---|---|---|---|---|
| PpDBF-2 | XmaI/EcoRV | PCR of original EST clone | | RC023 (SEQ ID NO:22) 5'ATCCCGGGACGCG ATGTCGGATGATGAG GTGA3' |
| | | | | RC024 (SEQ ID NO:23) 5'CTGATATCAGTCTA GGCTGAAGTGTCCAT TGT3' |
| PpDBF-3 | XmaI/EcoRV | PCR of original EST clone | | RC333 (SEQ ID NO:24) 5'ATCCCGGGCGTCGC AGTTTACGTGTGTTC ACC'3 |
| | | | | RC018 (SEQ ID NO:25) 5'CTGATATCTACCTA GTTCCTCTCTTCTTGC TTC'3 |
| PpLZ-2 | XmaI/SacI | 5'RACE and RT-PCR for FL clone | RC048 (SEQ ID NO:26): 5'GCCCGAGTCAT GGCGACTGCAGC AC3' | RC336 (SEQ ID NO:27) 5'ATCCCGGGTCAAG CTACGACGCCTCAAT CTTCC3' |
| | | | | RC337 (SEQ ID NO:28) 5'GCGAGCTCTCGTCA TCAGTTAGCATTGGC GTCGT3' |
| PpLZ-3 | XmaI/SacI | 5'RACE and RT-PCR for Full-length clone | RC060 (SEQ ID NO:29) 5'TAGCGCTCATG GGTGCGCATTGA AC3' | RC379 (SEQ ID NO:30) 5'ATCCCGGGAGTTCC TCCACATTTCCCGAC AATC3' |
| | | | | RC380 (SEQ ID NO:31) 5'GCGAGCTCGCCCTG AACTCTCGCTCTCGC TTG3' |

Tissue Harvest, RNA Isolation, and cDNA Library Construction

Canola and rice plants were grown under a variety of conditions and treatments, and different tissues were harvested at various developmental stages. Plant growth and harvesting were done in a strategic manner such that the probability of harvesting all expressable genes in at least one or more of the resulting libraries is maximized. The mRNA was isolated as described in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into *E. coli* were randomly picked and placed into microtiter plates.

Probe Hybridization

Plasmid DNA was isolated from the *E. coli* colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred via LIMS to a computer. Absolute identity was maintained by barcoding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

Gene Isolation

The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the *Physcomitrella patens* DBF-3 (SEQ ID NO:8) was blasted against proprietary contig databases of canola, rice, and soybean at E value of E-10. (Altschul, Stephen et al. Gapped BLAST and PSI_BLAST: a new generation of protein database search program. Nucleic Acids Res. 25: 3389–3402). All the contig hits were analyzed for the putative full length sequences, and the longest clones representing the putative full length contigs were fully sequenced. Three such contigs isolated from the proprietary contig databases are BnDBF-1, OsDBF-1, and OsDBF-2. The homology of the BnDBF-1, OsDBF-1, and OsDBF-2–1 amino acid sequences to the closest prior art is indicated in Table 6, Table 7, and Table 8, respectively.

TABLE 6

Degree of Amino Acid Identity and Similarity of BnDBF-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnDBF-1 | AAK93755 | Unknown protein | Arabidopsis thaliana | 75% | 81% |

TABLE 7

Degree of Amino Acid Identity and Similarity of OsDBF-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| OsDBF-1 | AAG51964 | Putative Transcriptional Regulator | Arabidopsis thaliana | 56% | 66% |

TABLE 8

Degree of Amino Acid Identity and Similarity of OsDBF-2 and a Similar Protein (Pair-wise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| OsDBF-2 | AAK93755 | Unknown protein | Arabidopsis thaliana | 59% | 70% |

Example 7

Engineering Stress-tolerant *Arabidopsis* Plants by Overexpressing the Genes LZ-3, DBF-2 and DBF-3 and Repressing LZ-2

Binary Vector Construction:

The pLMNC53 (Mankin, 2000, PhD thesis, University of North Carolina) vector was digested with HindIII (Roche) and blunt-end filled with Klenow enzyme and 0.1 mM dNTPs (Roche) according to the manufacturer's instructions. This fragment was extracted from agarose gel with a QIAquick Gel Extraction Kit (Qiagen) according to the manufacturer's instructions. The purified fragment was then digested with EcoRI (Roche) according to the manufacturer's instructions. This fragment was extracted from agarose gel with a QIAquick Gel Extraction Kit (Qiagen) according to the manufacturer's instructions. The resulting 1.4 kilobase fragment, the gentamycin cassette, included the NOS promoter, the aacCI gene, and the g7 terminator.

The vector pBlueScript was digested with EcoRI and SmaI (Roche) according to the manufacturer's instructions. The resulting fragment was extracted from an agarose gel with a QIAquick Gel Extraction Kit (Qiagen) according to the manufacturer's instructions. The digested pBlueScript vector and the gentamycin cassette fragments were ligated with T4 DNA Ligase (Roche) according to the manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and were grown overnight at 37° C. Plasmid DNA was extracted using the QIAprep Spin Miniprep Kit (Qiagen) following the manufacturer's instructions. Analyses of subsequent clones and restriction mapping was performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from an agarose gel with a QIAquick Gel Extraction Kit (Qiagen) according to the manufacturer's instructions. These two fragments were ligated with T4 DNA ligase (Roche) according to the manufacturer's instructions.

The resulting recombinant vector (pBPSJH001) was transformed into Top 10 cells (Invitrogen) using standard conditions. Transformed cells were selected on LB agar containing 100 mg/ml carbenicillin, 0.8 mg X-gal (5-bromo-4-chloro-3-indolyl-b-D-galactoside), and 0.8 mg IPTG (isopropylthio-b-D-galactoside), grown overnight at 37° C. White colonies were selected and used to inoculate 3 ml of liquid LB containing 100 mg/ml ampicillin and grown overnight at 37° C. Plasmid DNA was extracted using the QIAprep Spin Miniprep Kit (Qiagen) following the manufacturer's instructions. Analyses of subsequent clones and restriction mapping were performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

Subcloning of PpLZ-2, PpLZ-3, PpDBF-2, and PpDBF-3 into the Binary Vector

The fragments containing the different transcription factors were subcloned from the recombinant PCR2.1 TOPO vectors by double digestion with restriction enzymes (See Table 9) according to the manufacturer's instructions. The subsequent fragment was excised from agarose gel with a QIAquick Gel Extraction Kit (QIAgen) according to the manufacturer's instructions and ligated into the binary vectors pBPSJH001, cleaved with appropriate enzymes (See Table 9) and dephosphorylated prior to ligation. The resulting recombinant pBPSJH001 vector derivatives contained the transcription factors PpLZ-3, PpDBF-2, and PpDBF-3 in the sense orientation and PpLZ-2 in the antisense orientation under the control of the constitutive superpromoter.

TABLE 9

Listed are the names of the various constructs of the *Physcomitrella patens* transcription factors used for plant transformation

| Gene | Enzymes used to generate gene fragment | Enzymes used to restrict pBPSJH001 | Binary Vector Construct |
|---|---|---|---|
| PpLZ-2 | SmaI/Ecl136 | SmaI/Ecl136 | pBPSLVM017 |
| PpLZ-3 | XmaI/SacI | XmaI/Ecl136 | pBPSLVM067 |
| PpDBF-2 | XmaI/EcoRV | XmaI/Ecl136 | pBPSSH004 |
| PpDBF-3 | XmaI/EcoRV | XmaI/Ecl136 | pBPSLVM011 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 plants were grown and transformed according to standard conditions (Bechtold, 1993, Acad. Sci. Paris. 316:1194–1199; Bent et al., 1994, Science 265:1856–1860).

Screening of Transformed Plants

T1 seeds were sterilized according to standard protocols (Xiong et al., 1999, Plant Molecular Biology Reporter 17:159–170). Seeds were plated on ½ Murashige and Skoog media (MS) (Sigma-Aldrich), 0.6% agar, and supplemented with 1% sucrose, 150 µg/ml gentamycin (Sigma-Aldrich), and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1}$ $m^{-2}$ (white light; Philips TL 65 W/25 fluorescent tube) and 16 hours light and 8 hours dark day length cycle. Transformed seedlings were selected after 14 days and transferred to ½ MS media 0.6% agar plates, supplemented with 1% sucrose and allowed to recover for five-seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromol $s^{-1}m^{-2}$ (white light; Philips TL 65 W/25 fluorescent tube). The RH was then decreased to 60%, and the seedlings were desiccated further for eight hours. Seedlings were then removed and placed on ½ MS 0.6% agar plates supplemented with 2 µg/ml benomyl (Sigma-Aldrich) and 0.5 g/L MES (Sigma-Aldrich) and scored after five days.

Under drought stress conditions, PpDBF-3 overexpressing *Arabidopsis thaliana* plants showed a 42% survival rate (5 survivors from 12 stressed plants) to the stress screening, whereas the untransformed control showed a 6% survival rate (1 survivor from 18 plants). It is noteworthy that these analyses were performed with T1 plants. The results will be better when a homozygous, strong expresser is found.

Transgenic plants containing PpLZ-2, PpLZ-3, or PpDBF-2 are screened for their improved drought tolerance demonstrating that transgene expression confers drought tolerance.

TABLE 10

Summary of the drought stress tests

| | Drought Stress Test | | |
|---|---|---|---|
| Gene Name | Number of survivors | Total number of plants | Percentage of survivors |
| PpDBF-3 | 5 | 12 | 42% |
| Control | 1 | 18 | 6% |

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at –1.0° C., decreasing 1° C. per hour. The seedlings were then incubated at –5.0° C. for 24 hours and then allowed to thaw at 5° C. for 12 hours. The water was poured off, and the seedlings were scored after 5 days.

PpLZ-3 over-expressing *Arabidopsis thaliana* plants showed a 40% survival rate (4 survivors from 10 stressed plants); whereas the untransformed control showed a 0% survival rate (0 survivors from 22 tested plants). It is noteworthy that these analyses were performed with T1 plants. The results will be better when a homozygous, strong expresser is found.

Transgenic plants containing PpLZ-2, PpDBF-2, or PpDBF-3 are screened for their improved cold tolerance demonstrating that transgene expression confers cold tolerance.

TABLE 11

Summary of the freezing stress tests

| | Freezing Stress Test | | |
|---|---|---|---|
| Gene Name | Number of survivors | Total number of plants | Percentage of survivors |
| PpLZ-3 | 4 | 10 | 40% |
| Control | 0 | 22 | 0% |

Salt Tolerance Screening

Seedlings are transferred to filter paper soaked in ½ MS and placed on ½ MS 0.6% agar supplemented with 2 µg/ml benomyl the night before the salt tolerance screening. For the salt tolerance screening, the filter paper with the seedlings is moved to stacks of sterile filter paper, soaked in 50 mM NaCl, in a petri dish. After two hours, the filter paper with the seedlings is moved to stacks of sterile filter paper, soaked with 200 mM NaCl, in a petri dish. After two hours, the filter paper with the seedlings is moved to stacks of sterile filter paper, soaked in 600 mM NaCl, in a petri dish. After 10 hours, the seedlings are moved to petri dishes containing ½ MS 0.6% agar supplemented with 2 µg/ml benomyl. The seedlings are scored after 5 days.

The transgenic plants are screened for their improved salt tolerance, demonstrating that transgene expression confers salt tolerance.

Example 8

Detection of the LZ-2, LZ-3, DBF-2 and DBF-3 Transgenes in the Transgenic Arabidopsis Lines One leaf from a wild type plant and one leaf from a transgenic Arabidopsis plant were homogenized in 250 µl Hexadecyltrimethyl ammonium bromide (CTAB) buffer (2% CTAB, 1.4 M NaCl, 8 mM EDTA, and 20 mM Tris pH 8.0) and 1 µl β-mercaptoethanol. The samples were incubated at 60–65° C. for 30 minutes and 250 µl of chloroform was then added to each sample. The samples were vortexed for 3 minutes and centrifuged for 5 minutes at 18,000×g. The supernatant was taken from each sample, and 150 µl isopropanol was added. The samples were incubated at room temperature for 15 minutes, and centrifuged for 10 minutes at 18,000×g. Each pellet was washed with 70% ethanol, dried, and resuspended in 20 µl TE. Then, 2.5 µl of the above suspension was used in a 50 µl PCR reaction using Taq DNA polymerase (Roehe Molecular Biochemicals) according to the manufacturer's instructions. Binary vector plasmid with each gene cloned in was used as positive control, and the wild type C24 genomic DNA was used as negative control in the PCR reactions. Ten microliters of each PCR reaction was analyzed on 0.8% agarose/ethidium bromide gel. The PCR program for LZ-2, DBF-2, and DBF-3 detection was as follows: 1 cycle of 1 minute at 94° C., 1 minute at 75° C. and 3 minutes at 72° C., followed by 14 cycles of the same cycle except that the annealing temperature decreased 1° C. every cycle until 62° C.; and then 16 cycles of 1 minute at 94° C., 1 minute at 62° C., and 3 minutes at 72° C. The PCR program for LZ-3 was 35 cycles of 1 minute at 94° C., 30 seconds at 62° C., and 1 minute at 72° C., followed by 5 minutes at 72° C. The gene-specific primers, and the size of the amplified bands (Gene Product Size) are listed below.

```
PpLZ-2:                                      (SEQ ID NO:27)
RC336:   5'ATCCCGGGTCAAGCTACGACGCCTCAATCTTCC3' and (SEQ ID NO:28)
RC337:   5'GCGAGCTCTCGTCATCAGTTAGCATTGGCGTCGT3'.

PpLZ-3:                                      (SEQ ID NO:32)
RC1183:  5'GCACCGAGGAGCTGCGTGCGATGAA 3' and (SEQ ID NO:33)
RC1184:  5'CGCTTAAGGTCACCGCCTGGTAGG 3'.

PpDBF-2                                      (SEQ ID NO:22)
RC023:   5'ATCCCGGGACGCGATGTCGGATGATGAGGTGA3' and (SEQ ID NO:23)
RC024:   5'CTGATATCAGTCTAGGCTGAAGTGTCCATTGT3'.

PpDBF-3                                      (SEQ ID NO:24)
RC333:   5'ATCCCGGGCGTCGCAGTTTACGTGTGTTCACC 3' and (SEQ ID NO:25)
RC018:   5'CTGATATCTACCTAGTTCCTCTCTTCTTGCTT 3'.
```

The transgenes were successfully amplified from the T1 transgenic lines, but not from the wild type C24. This result indicates that the T1 transgenic plants contain at least one copy of the transgenes. There was no indication of existence of either identical or very similar genes in the untransformed Arabidopsis thaliana control which could be amplified by this method.

Example 9

Detection of the LZ-2, LZ-3, DBF-2, and DBF-3 Transgene mRNA in Transgenic Arabidopsis Lines Transgene expression was detected using RT-PCR. Total RNA was isolated from stress-treated plants using a procedure adapted from (Verwoerd et al., 1989, Nuc. Acids Res. 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH 8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $1/10^{th}$ volume 3 M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water.

To remove contaminating DNA from the samples, each was treated with RNase-free DNase (Roche) according to the manufacturer's recommendations. cDNA was synthesized from total RNA using the Superscript First Strand cDNA Synthesis System for RT-PCT (Gibco-BRL) following the manufacturer's recommendations. PCR amplification of a gene-specific fragment from the synthesized cDNA was performed using Taq DNA polymerase (Roche) and gene-specific primers (See Example 8 for primers) in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad). Expression of the transgenes was detected in the T1 transgenic line.

These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 8.

Example 10

Engineering Stress-Tolerant Soybean Plants by Over-Expressing the LZ-2, LZ-3, DBF-2 or DBF-3 Gene The constructs pBPSLVM017, pBPSLVM067, pBPSSH004, and pBPSLVM011 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacterial culture is pelleted at 7000 rpm for 7 minutes at room temperature, and resuspended in MS (Murashige and Skoog, 1962) medium supplemented with 100 µM acetosyringone. Bacterial cultures are incubated in this pre-induction medium for 2 hours at room temperature before use. The axes of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *Agrobacteria*. The liquid medium is used to moisten the sterile filter paper. The embryos are incubated during 4 weeks at 25° C., under 150 µmol m$^{-2}$sec$^{-1}$ and 12 hours photoperiod. Once the seedlings produce roots, they are transferred to sterile metromix soil. The medium of the in vitro plants is washed off before the plants are transferred to soil. The plants are kept under a plastic cover for 1 week to favor the acclimatization process. Then the plants are transferred to a growth room where they are incubated at 25° C., under 150 µmol m$^{-2}$sec$^{-1}$ light intensity and 12 hours photoperiod for about 80 days.

The transgenic plants are screened for their improved drought, salt, and/or cold tolerance according to the screening method described in Example 7, demonstrating that transgene expression confers stress tolerance.

Example 11

Engineering Stress-tolerant Rapeseed/Canola Plants by Over-expressing the LZ-2, LZ-3, DBF-2, or DBF-3 Gene The constructs pBPSLVM017, pBPSLVM067, pBPSSH004, and pBPSLVM011 are used to transform rapeseed/canola as described below.

The method of plant transformation described herein is applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed, and the seeds are air dried overnight in a half-open sterile Petri dish. During this period, the seeds lose approximately 85% of their water content. The seeds are then stored at room temperature in a sealed Petri dish until further use.

DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are screened for their improved stress tolerance according to the screening method described in Example 7, demonstrating that transgene expression confers stress tolerance.

Example 12

Engineering Stress-tolerant Corn Plants by Over-expressing the LZ-2, LZ-3, DBF-2 or DBF-3 Gene The constructs pBPSLVM017, pBPSLVM067, pBPSSH004, and pBPSLVM011 are used to transform corn as described below.

Transformation of maize (*Zea Mays* L.) is performed with the method described by Ishida et al., 1996, Nature Biotech. 14745–50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are screened for their improved drought, salt, and/or cold tolerance according to the screening method described in Example 7, demonstrating that transgene expression confers stress tolerance.

Example 13

Engineering Stress-tolerant Wheat Plants by Over-expressing the LZ-2, LZ-3, DBF-2, or DBF-3 Gene The constructs pBPSLVM017, pBPSLVM067, pBPSSH004, and pBPSLVM011 are used to transform wheat as described below.

Transformation of wheat is performed with the method described by Ishida et al., 1996, Nature Biotech. 14745–50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are screened for their improved stress tolerance according to the screening method described in Example 7, demonstrating that transgene expression confers stress tolerance.

Example 14

Monitoring Changes in mRNA Concentration of PpLZ-2, PpDBF-2, and PpDBF-3 in Cold Treated *Physcomitrella patens* Cultures DNA Microarray Slide Preparation PCR amplification was performed in 96 well plates from selected *Physcomitrella patens* ESTs cloned in the pBluescript vector. The PCR buffer set (Boehringer Mannheim) was employed for the PCR reaction. Each PCR reaction mixture contains 10 µl of PCR Buffer without MgCl$_2$, 10 µl of MgSO$_4$, 3 µl of SK-Fwd primer (MWG-Biotech, Sequence: 5'-CGCCAAGCGCGCAATTAACCCTCACT-3') (SEQ ID NO:34), 3 µl SK-Rev primer (MWG-Biotech, Sequence: 5'GCGTAATACGACTCACTA TAGGGCGA-3') (SEQ ID NO:35), 2 µl dNTP, 1 µl Taq DNA polymerase (Roche), 72 µl water and 1 µl DNA template. After denaturing at 95° C. for three minutes, the PCR reactions were performed with 35 cycles of three consecutive steps including: denaturing at 95° C. for 45 seconds, annealing at 63° C. for 45 seconds, and elongation at 72° C. for 60 seconds. The last elongation was at 72° C. for 10 minutes. The PCR products were then purified with QIAquick PCR purification kit (Qiagen, Inc.), eluted with water and the DNA concentration measured at 260 nm in a spectrophotometer.

Two to five µg of each PCR product were dried down and dissolved in 50 µl of DMSO. The PCR products were then formatted from 96 well plates to 384 well plates for printing. The Microarray GenIII arrayer (Molecular Dynamics) was employed to print the PCR products to microarray slides (Molecular Dynamics) with the format recommended by the manufacturer. The printed spots were about 290 µm in diameter and were spaced about 320 µm from center to center. After printing, the slide was left in the dust free chamber for one hour to dry. UV cross-linking was performed with 600 µJ/mm. The cross-linked slides were ready for hybridization and were stored in dark and dry chambers.

Microarray Probe Synthesis

Total RNA was extracted from cold-treated *Physcomitrella patens* cultures (12 hours at 4° C. in the dark) following the RNA extraction method described in Ausubel et al. (Curr. Prot. in Mol. Biol., 1987, J. Wiley and Sons, New York).

Oligotex mRNA midi kit (Qiagen Inc.) was applied to isolate the mRNA from total RNA with an approach combining both batch and standard protocol as recommended by the manufacturer. After binding the total RNA with Oligotex, the sample was centrifuged at 14000×g to separate the Oligotex:mRNA with the liquid phase instead of running through a column. After four washes with OW2 buffer as described in batch protocol, the Oligotex:mRNA was resuspended in 400 µl OW2 and then collected by the column as the standard protocol. The mRNA was eluted following standard protocol.

Cy3 and Cy5 labeled cDNA probes were synthesized from mRNA with Superscript Choice System for cDNA synthesis (Gibco BRL). Both oligo-(dT)$_{25}$ primer (Genosys Biotechnologies) and Nonamer primer (Amersham Pharmacia Biotech) were mixed with mRNA to reach a total volume of 20 µl. The mixture was first heated at 70° C. for 10 minutes and then left at room temperature for 15 minutes before transferring to ice. Once the sample is on ice, the following was added: 8 µl First Strand Synthesis Buffer, 4 µl 0.1 M DTT, 2 µl dNTP (Amersham Pharmacia Biotech), 2 µl Cy3- or Cy5-dCTP (Amersham Pharmacia Biotech), 2 µl RNase Inhibitor (Gibco BRL), and 2 µl SuperScript II Reverse Transcriptase. The first strand synthesis was performed at 42° C. for 8 hours, and the mixture was then heated at 94° C. for three minutes after the reaction.

After the first strand synthesis, 4 µl of 2.5 M sodium hydroxide was added to the reaction and the mixture was incubated at 37° C. for ten minutes. Then, 20 µl of 2M MOPS (pH 5.0) and 500 µl of PB buffer (Qiagen Inc.) were added to each reaction. The probe was then purified by the QIAquick PCR Purification Kit (Qiagen Inc.) with the protocol provided by the manufacturer.

cDNA Microarray Hybridization and Washes

The purified Cy3- and Cy5-labeled probes were mixed and vacuum dried to give a final volume of 9 µl. Then, 9 µl Microarray Hybridization Solution (Amersham Pharmacia Biotech) and 18 µl Formamide (Sigma) were added to the cDNA probes to give a final volume of 36 µl. The mixture was applied to the printed microarray slide which was then covered with a clean dust-free cover slide, ensuring no air was trapped. The hybridization was performed in a hybridization chamber at 42° C. for 16 to 20 hours. After the hybridization, the slides were washed two times with 0.5× SSC, 0.2% SDS at room temperature for 5 minutes and 15 minutes. Stringent washes were performed twice with 0.25× SSC, 0.1% SDS at 55° C. for 10 and 30 minutes, respectively. After the washes, the slides were briefly rinsed with Millipore water and dried under compressed nitrogen.

Scanning and Microarray Data Analysis

The cDNA microarrays were scanned using the microarray GenIII Scanner (Molecular Dynamics) equipped with two laser channels. The scanned images were first viewed and adjusted in ImageQuant software (Molecular Dynamics) and then were analyzed by ArrayVision software (Molecular Dynamics). The signal intensity for each spot was extracted by ArrayVision software (Molecular Dynamics) and transferred to Excel (Microsoft). The data obtained was normalized by dividing the difference of the intensity value and background and the difference of the control value and background. The ratio was then obtained by dividing the normalized data.

The transcript level of PpLZ-2 decreased 3 fold and the transcript levels of PpDBF-2 and PpDBF-3 increased 2–5 fold and 5 fold when compared to untreated controls, respectively (See Table 12).

TABLE 12

Summary of the Microarray Experiments

| Gene Name | Fold Repression | Fold Induction |
|---|---|---|
| PpLZ-2 | 3 | — |
| PpDBF-2 | — | 3.5 |
| PpDBF-3 | — | 5 |

Example 15

Identification of Homologous and Heterologous Genes

The disclosed gene sequences can be used to identify genes from cDNA or genomic libraries that are homologous or heterologous to LZ-2, LZ-3, DBF-2, DBF-3, BnDBF-1, OsDBF-1, or OsDBF-2. Homologous genes (e.g. full-length cDNA clones) can be isolated via nucleic acid hybridization using, for example, cDNA libraries. Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. In aqueous solution hybridization and washing is performed at an ionic strength of 1 M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only in a distinct domain of (for example 10–20 amino acids) can be carried out by using synthetic radiolabeled oligonucleotide probes. Radiolabeled oligonucleotides are prepared by phosphorylation of the 5-prime end of two complementary oligonucleotides with T4 protein kinase. The complementary oligonucleotides are annealed and ligated to form concatemers. The double stranded concatemers are then radiolabeled by, for example, nick transcription. Hybridization is normally performed at low stringency conditions using high oligonucleotide concentrations.

Oligonucleotide hybridization solution:
6× SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5–10° C. below the estimated oligonucleotide $T_m$ or down to room temperature followed by washing steps and autoradiography. Washing is performed with low stringency such as 3 washing steps using 4×SSC. Further details are described by Sambrook, J. et al., 1989, "Molecular Cloning: A Laboratory Manual", Cold Spring Harbor Laboratory Press or Ausubel, F. M. et al., 1994, "Current Protocols in Molecular Biology," John Wiley & Sons.

Example 16

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni—NTA affinity chromatography (Qiagen). Recombinant proteins are then used to produce specific antibodies, for example, by using standard techniques for rabbit immunization. Antibodies are affinity purified using a Ni—NTA column saturated with the recombinant antigen as described by Gu et al., 1994, BioTechniques 17:257–262. The antibody can be used to screen expression cDNA libraries to identify homologous or heterologous genes via an immunological screening (Sambrook, J. et al., 1989, "Molecular Cloning: A Laboratory Manual," Cold Spring Harbor Laboratory Press or Ausubel, F. M. et al., 1994, "Current Protocols in Molecular Biology," John Wiley & Sons).

Example 17

In vivo Mutagenesis

In vivo mutagenesis of microorganisms can be performed by passage of plasmid (or other vector) DNA through *E. coli* or other microorganisms (e.g. *Bacillus spp.* or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277–94, ASM: Washington.). Such strains are well known to those skilled in the art. The use of such strains is illustrated, for example, in Greener, A. and Callahan, M., 1994, Strategies 7:32–34.

Transfer of mutated DNA molecules into plants is preferably done after selection and testing in microorganisms. Transgenic plants are generated according to various examples within the exemplification of this document.

Example 18

In vitro Analysis of the Function of *Physcomitrella Genes* in *Transgenic* Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N. C., Stevens, L., 1982, Fundamentals of Enzymology. Oxford Univ. Press: Oxford; Boyer, P. D., ed., 1983, The Enzymes, $3^{rd}$ ed. Academic Press: New York; Bisswanger, H., 1994, Enzymkinetik, $2^{nd}$ ed. VCH: Weinheim (ISBN 3527300325); Bergmeyer, H. U., Bergmeyer, J., Graβl, M., eds., 1983–1986, Methods of Enzymatic Analysis, $3^{rd}$ ed., vol. I–XII, Verlag Chemie: Weinheim; and Ullmann's Encyclopedia of Industrial Chemistry, 1987, vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al., 1995, EMBO J. 14: 3895–3904 and references cited therein). Reporter gene test systems are well known and established for applications in both prokaryotic and eukaryotic cells, using enzymes such as β-galactosidase, green fluorescent protein, and several others.

The determination of activity of membrane-transport proteins can be performed according to techniques such as those described in Gennis, R. B., 1989, Pores, Channels and Transporters, in Biomembranes, Molecular Structure and Function, pp. 85–137, 199–234 and 270–322, Springer: Heidelberg.

Example 19

Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernatant fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F., 1986, Biochemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133–140; Malakhova et al., 1996, Biotekhnologiya 11:27–32; Schmidt et al., 1998, Bioprocess Engineer 19:67–70; Ulmann's Encyclopedia of Industrial Chemistry, 1996, vol. A27, VCH: Weinheim, p. 89–90, p. 521–540, p. 540–547, p. 559–566, 575–581, and p. 581–587; Michal, G., 1999, Biochemical Pathways: An Atlas of Biochemistry and Molecular Biology, John Wiley and Sons; Fallon, A. et al., 1987, Applications of HPLC in Biochemistry in: Laboratory Techniques in Biochemistry and Molecular Biology, vol. 17.

APPENDIX

Nucleotide sequence of the partial LZ-2 from
Physcomitrella patens (SEQ ID NO:1)
GCACCAGGAGGAGCCTTACATCAGTGCAGCCGAGCTTCGATTATATCCTCA

CTCCGGAAGCTCAGATTTCTCCGCGCCCATGGGGACAAGTGAGGAACTTCA

GGTTGTGCACGAGCAACGATCCGAGTGTTGTAGTGGAGGGCGCGTTGAACC

CTTTGTTCTCAGGTATGCGTGACGACAATGAAGCGATTACTGCCCATGCTC

GAATAGCCGGTAACCCTGTCGCGCCTGACACCCTGGATGGGGTTAGATATC

CCCAGGAATACGAATACATTTTAAAACACAAGCTGGAGATGGCTTGTGCTG

CAGTCGCCATGACTCGGGCAAAGGCAAGACAGACAAGAGGATCAGCGGAAG

CTAGTGTTGGGCGAGCAGAACCATCACCAAAAATCCAAGCATCTGGAACAC

TTCCTCCGAAAGGAAAAACATCAGCTTGTAACCTTCCTGCTGCGGAGAAAT

CCGATGCAGATGTGGGAAAGAGTCGACCAATCACCAGCGGCTCGGAAGTCT

CTGAAGATGAAGAACATGACGAGCAGAACGGAAAGACAGCACCTGGTGACA

TCAAACGCGTCAAGAGGATGCTGTCTAACCGCGAATCTGCCAGAAGATCTC

GTAAAGAAAACAGGCCA

APPENDIX-continued

Nucleotide sequence of the full-length LZ-2 from
Physcomitrella patens (SEQ ID NO:2)
GCCCTTATCCCGGGTCAAGCTACGACGCCTCAATCTTCCCCCCAATCTCCC

CCCCAAGATATGGAACACTCATCTTCCGTCGACGATCTCGTGGGCACATTC

TGGGACGATTCTGCCGATCTTGTAGACAAGGCAGCAGCATCCACGACGATT

AACAGGAGTGCATCCGAATGGTCTTTTCAAGAATTTCTTAAAGACAGCCAC

TCCGCTGCCGCTGGCCCAGGGGCCCTCAAGCTGCGGCCTGCTTGCAAGAGC

CGGTTCCTGATGGAGCATGGCGATGTCAAGGTGTGCGAACCCGAGGCACAG

AAAGTGAAGGAATCTCTCAGGGCTGAGGAGGAAGATGTAGGTGAGGAGCCT

TACATCAGTGCAGCCGAGCTTCGATTATATCCTCACTCCGGAAGCTCAGAT

TTCTCCGCGCCCATGGGGACAAGTGAGGAACTTCAGGTTGTGGACGACAAC

GATCCGAGTGTTGTAGTGGAGGGCGCGTTGAACCCTTTGTTCTCAGGTATG

CGTGACGACAATGAAGCGATTACTGCCCATGCTCGAATAGCCGGTAACCCT

GTCGCGCCTGACACCCTGGATGGGGTTAGATATCCCCAGGAATACGAATAC

ATTTTAAAACACAAGCTGGAGATGGCTTGTGCTGCAGTCGCCATGACTCGG

GCAAAGGCAAGACAGACAAGAGGATCAGCGGAAGCTAGTGTTGGGCGAGCA

GAACCATCACCAAAAATCCAAGCATCTGGAACACTTCCTCCGAAAGGAAAA

ACATCAGCTTGTAACCTTCCTGCTGCGGAGAAATCCGATGCAGATGTGGGA

AAGAGTCGACCAATCACCAGCGGCTCGGAAGTCTCTGAAGATGAAGAACAT

GACGAGCAGAACGGAAAGACAGCACCTGGTGACATCAAACGCGTCAAGAGG

ATGCTGTCTAACCGCGAATCTGCCAGAAGATCTCGTAGAAGAAAACAGGCC

CATTTGAGTGAGCTGGAAATGCAGGTAGCTCAATTGAGGGTTGAGAATACA

AATCTGTTGCAGAGACTCCAAGATATCAGTCAAAAGTTCCAAGAAGCAGCT

ATTGACAATCGTGTTCTCACGGCAGATTGCGAAGCCTTACGTGCCAAGGTG

AATATGGCAGCACGAGATTTGATGGCGAGGCATGGACAAATTCCTGGTGGA

CAATTTATCTTGGAACCCAGCTTGAGATATGTGTTGCCTTACGAAATGCAG

CCCGTCGCCGATGAATCCGCGCAGTATATGCAGCAGGTAAAGGAAAATACT

CCTTTAGCACACCAGGATCACCAACAGAGTAGTACTGGTCTGGGTAAGATG

GGACGTACCCCGTCGATGCAGCGCGTTGCCAGCTTGGAGCATCTGCAGAAG

CGCATCCGGAGCGGCGTGACTTGCAACACTCCCTCCGGGAACAGCTACTGG

GAGATGGAGGGCCCAGCCATGGTGGAACAACATGACATCTAAACAATTGAT

TTCTTAAGAGTTTCGTTTTTACTAAGTTTGTTATTATAATTGTGTTTAAAC

TATATTGCTGTGACTCACTCCACGACGCCAATGCTAACTGATGACGAGAGC

TCGCAAGGGC

Deduced amino acid sequence of LZ-2 from
Physcomitrella patens (SEQ ID NO:3)
MEHSSSVDDLVGTFWDDSADLVDKAAASTTINRSASEWSFQEFLKDSHSAA

AGPGALKLRPACKSRFLMEHGDVKVCEPEAQKVKESLRAEEEDVGEEPYIS

AAELRLYPHSGSSDFSAPMGTSEELQVVDDNDPSVVVEGALNPLFSGMRDD

NEAITAHARIAGNPVAPDTLDGVRYPQEYEYILKHKLEMACAAVAMTRAKA

RQTRGSAEASVGRAEPSPKIQASGTLPPKGKTSACNLPAAEKSDADVGKSR

APPENDIX-continued

PITSGSEVSEDEEHDEQNGKTAPGDIKRVKRMLSNRESARRSRRKQAHLSE

LEMQVAQLRVENTNLLQRLQDISQKFQEAAIDNRVLTADCEALRAKVNMAA

RDLMARHGQIPGGQFILEPSLRYVLPYEMQPVADESAQYMQQVKENTPLAH

QDHQQSSTGLGKMGRTPSMQRVASLEHLQKRIRSGVTCNTPSGNSYWEMEG

PAMVEQHDI*

Nucleotide sequence of the partial LZ-3 from
Physcomitrella patens (SEQ ID NO:4)
GCACGAGCCAAAATGATGCGGATAAAAAATATTCCAATTTCCCCTCTGCTG

CGTTATCTGCGGGTGACTGTGGTGGTCAAGACTATGAGGACATCCTTAAGC

AGAAGTTGGAAAGGGCGTGCGCTGCAGCGGCTCTCTCTAGAGTGAATGGCG

AGGGTGCAATAATCGGCACCAGATCGGTTGGAGCTATTTGTCAGAAGAGTT

TTGCTATCGAATCATCTGCCGCTAGTGCTTGTCCAAGTGGAGTTCAATGCG

CACCCATGAGCGCTAAGTCTCCTTCTCCAAAACCTGAAGTGGATGCATCAA

CCGGGAAGGTCAAACTTACGACCAGTGGTTCGGAACTTTCTGATGACGACG

AACATGATTTGTTTAAACCAAAGCCTACCAGGCGGTGACCTTAAGCGTGTG

AAGAGAATGTTGTCAAACCGTGAATCTGCCCGACGCTCGCGCAGAAGGAAA

CAGGCACACTTGAGTGATCTAGAAATGCAGGTTGCGCAATTGCGAGTTGAA

AATACTACGCTTATGCAAAGATTGCAAGAGATTACCCACATGCATAAAGAT

GCATCTGTCGACAACCGAATTCTAAAGGCAGATGTGGAGGCGTTGCGTGCT

AAGGTGAAAATGGCTGAAGACATGGTGGCCCGTCAAGGACAGCCCATGTCA

AATCTCATTCCCGACCCAGTTTAAGCTTTATGACACCGTTCAATGTGAATG

ATATGGAAGACCATTTCTGCAACA

Nucleotide sequence of the full-length LZ-3 from
Physcomitrella patens (SEQ ID NO:5)
ATCCCGGGAGTTCCTCCACATTTCCCGACAATCTATTTTTCTTTAGAATAT

GGATCGCATATCTTCCGTTGACGACATCCTGAGCGCATACTGGAACGAGTC

GTCTATGACTTCTCCTGTGAAGGGCAGCATGAACCGCAGTGCTTCTGAGTT

CGCTTTTCAAGAATTTATTAAGGAGAACATGACTGCCACATCTTGCTTCGG

AGGCCGCTCCAAGAGCCGCTTCTATCAATCGCAGGCGGATGAGGGGAAAGC

TCTTAACGATCAAAGTCGTGACAATCTTATGATCTCGGCAAAATCTGAATC

AGAGTTCACTCCTCCGATGTTCGCAAGCACCGAGGAGCTGCGTGCGATGAA

TAACGTCGTGGACCCTGTTGAAGTCGACGATATTGTGGGGATTGAGGGGGC

GCTGAACCCCCTCTTCTCCCGTGTCCAAAATGATGCGGATAAAAAATATTC

CAATTTCCCCTCTGCTGCGTTATCTGCGGGTGACTGTGGTGGTCAAGACTA

TGAGGACATCCTTAAGCAGAAGTTGGAAGGGCGTGCGCTGCAGCGGCTCT

CTCTAGAGTGAATGGCGAGGGTGCAATAATTGGACAATCGGTTGGAGCTAT

TTGTCAGAAGAGTTTTGCTATCGAATCATCTGCCGCTAGTGCTTGTCCAAG

TGGAGTTCAATGCGCACCCATGAGCGCTAAGTCTCCTTCTCCAAAACCTGA

AGTGGATGCATCAACCGGGAAGGTCAAACTTACGACCAGTGGTTCGGAACT

TTCTGATGACGACGAACATGATTTGTTAAACCAAAGCCTACCAGGCGGTGA

CCTTAAGCGTGTGAAGAGAATGTTGTCAAACCGTGAATCTGCCCGACGCTC

GCGCAGAAGGAAACAGGCACACTTGAGTGATCTAGAAATGCAGGTTGCGCA

APPENDIX-continued

ATTGCGAGTTGAAAATACTACGCTTATGCAAAGATTGCAAGAGATTACCCA

CATGCATAAAGATGCATCTGTCGACAACCGAATTCTAAAGGCAGATGTGGA

GGCGTTGCGTGCTAAGGTGAAAATGGCTGAAGACATGGTGGCCCGTCAAGG

ACAGCCCATGTCAAATCTCATTCCCGACCCCAGTTTAAGCTTTATGACACC

GTTCAATGTGAATGATATGGAAAGACCATTTCTGCAACAGATGAGGCACAG

TTCCATGCTACGCCATGATCAGCAACAGCAGCCTGCTAGTGGCATTAGGGG

TAAGATGGGACGTGCACCTTCAATGCAACGGGTTGCCAGCCTGGAGCATCT

GACGAAGCGTATCCGCAACGGGAGTTCCTGCAACGTACCGGCTTGGGGTGG

CTGGGACATGGACAGACCTGCCATGGTACAGGAACACGGCATCTGATCAAT

GTTTCCGCGCTGACTATGTAGTAGAATCGATGTAACTTACATTTACTCCGC

TTATTTCAAGCGAGAGCGAGGTTCAGGGCGAGCTCGC

Deduced amino acid sequence of LZ-3 from
Physcomitrella patens (SEQ ID NO:6)
MDRISSVDDILSAYWNESSMTSPVKGSMNRSASEFAFQEFIKENMTATSCF

GGRSKSRFYQSQADEGKALNDQSRDNLMISAKSESEFTPPMFASTEELRAM

NNVVDPVEVDDIVGIEGALNPLFSRVQNDADKKYSNFPSAALSAGDCGGQD

YEDILKQKLGRACAAAALSRVNGEGAIIGQSVGAICQKSFAIESSAASACP

SGVQCAPMSAKSPSPKPEVDASTGKVKLTTSGSELSDDDEHDLLNQSLPGG

DLKRVKRMLSNRESARRSRRRKQAHLSDLEMQVAQLRVENTTLMQRLQEIT

HMHKDASVDNRILKADVEALRAKVKMAEDMVARQGQPMSNIPDPSLSFMTP

FNVNDMERPFLQQMRHSSMLRHDQQQQPASGIRGKMGRAPSMQRVASLEHL

TKRIRNGSSCNVPAWGGWDMDRPAMVQEHGI*

Nucleotide sequence of the partial DBF-2 from
Physcomitrella patens (SEQ ID NO:7)
TACCTTCTGAATGCATCGTCACGTCTGTTCTCTTTCCAGGCCTGATAGCGA

AGCGCAACTTCTGGCAGCTGTATGAGCAGCAGCCAGTACATCGCGGCACGA

CCAGTTACAGGTCCTTCGCTAAGAACATGGGTGTGTGCAACGACGGCTATA

AAACCATCAACATGGCAGCCTAGATCTATTTTGACAATGTCATTTGCTGCA

AGAAACAGATTCGTCGCTGGCCAAAGGCGAGAAGTGGCATACGGTGTTGTTG

ACAGAGACACAAGTGGGAAATGCAACTCCCTTGTCAATTTTTTTCTTGGAG

TTCTTGTACATGAGCGCTGTTAGATCGCGAATCGAAGAATCGCCCTTCTCG

CAAAGGTCGACGATCTTCGCTCCTGGCTTGCAATCGGCCAGGACTGCTTGC

AAGGCCTTGTTAGCGACCTCGGCCGCGCACTTATACTTGGTGACGACATCC

GGCGACGTCAAGTCGAGCTCCTTCTCCTCTTTCACCTCATCATCCGACATC

GCGTCACGCGGGTTTCAAAACAAAACCGAGCTCCTCTCAACTCCTGACCCT

CACTGCCTTGAACAGGTAGAAAACGCAGCTCAGTCACCTCAACACGGCTCT

GAGCAATGCGCAAGACGAAAAAAAAATCTACAACTGAGGCCACCGTGTAGC

AGAGCAAAAGAGGGGGTGTCCGAGAACGCTCGTGCCAGGGAACGACAGACA

ACGATGCAGGGGCTCCGCCGAGGACTTGTGTCAAGCTGGTGC

APPENDIX-continued

Nucleotide sequence of the full-length DBF-2 from
*Physcomitrella patens* (SEQ ID NO:8)
GGCACCAGCACCCCCTCTTTTGCTCTGCTACACGGTGGCCTCAGTTGTAGA

TTTTTTTTTCGTCTTGCGCATTGCTCAGAGCCGTGTTGAGGTGACTGAGCT

GCGTTTTCTACCTGTTCAAGGCAGTGAGGGTCAGGAGTTGAGAGGAGCTCG

GTTTTGTTTTGAAACCCGCGTGACGCGATGTCGGATGATGAGGTGAAAGAG

GAGAAGGAGCTCGACTTGACGTCGCCGGATGTCGTCACCAAGTATAAGTGC

GCGGCCGAGGTCGCTAACAAGGCCTTGCAAGCAGTCCTGGCCGATTGCAAG

CCAGGAGCGAAGATCGTCGACCTTTGCGAGAAGGGCGATTCTTCGATTCGC

GATCTAACAGCGCTCATGTACAAGAACTCCAAGAAAAAAATTGACAAGGGA

GTTGCATTTCCCACTTGTGTCTCTGTCAACAACACCGTATGCCACTTCTCG

CCTTTGGCCAGCGACGAATCTGTTCTTGCAGCAAATGACATTGTCAAAATA

GATCTAGGCTGCCATGTTGATGGTTTTATAGCCGTCGTTGCACACACCCAT

GTTCTTAGCGAAGGACCTGTAACTGGTCGTGCCGCGGATGTTCTGGCTGCT

GCTCATACAGCTGCAGAAGTTGCGCTTCGCCTAGTCAGGCCTGGAAAGAAG

AACAAGGACGTGACCGATGCAATTCAGAAGGTAGCGGCTGCCTACGATTGC

AAGATTGCCGAGGGTGTGTTGAGTCATCAGCTCAAGCAGTTTGTCATCGAT

GCTAACAAAGTAATCCTGAGTGTATCGAACCCTGAAACGCGTGTAGATGAT

GCCGAGTTCGAGGAAAACGAGGTCTATGCAATTGACATCGTGACCAGTACG

GGTGATGGAAAGCCCAAGTTGTTAGATGAGAAGCAGACCACAGTGTATAAG

AGGGCTGTGGACAAGAATTATCACCTGAAAATGAAGGCATCAAGATTCATC

TTCAGCGAAATCAATACCAAGTTCCCTATTATGCCTTTCACTGCTAGAGCT

CTAGAAGAGAAGAGGGCCCGCCTTGGTATCGTGGAGTGTGTTAACCATGAA

CTGCTTCAGCCCTACCCTGTTCTTCACGAAAAGCCCGGTGACTGCGTAGCC

CACATTAAGTTCACTGTATTGCTCATGCCCAACGGATCCGATAAGATAACT

GGTCTGCCACTTCAAGAATGTCAGTCGACCAAAGTTCCCGAGGACCCAGAG

ATCAAAGCTTGGTTGGCTTTGGGTACTAAGTCCAAAAAGAAGGGTGGTGGT

AAGAAGAAAAAAGGTAAGAAAGGCGACGCCATGATTGAGGACTCGTCTGAA

ACAGCCGCAGAGTCAGCCACAGGAACTACTGATACAATGGACACTTCAGCC

TAGACTTCACAGAACAGAGTGGATTGAGAGTCGTACCCATGCACCATTTCA

CGAACCCTAAACTCCGTGCAGTCTAAGTTCCATCTCTGGTGCTCATATTCG

TGCACCATTTCAGTTTTGCTCCTGACTCTAGCGATAGTCCTGTCTGGTAAC

CATACAACCTATTGGACATATCCCGACAATGCTGTTGCTTGTTCAAATCCC

TGTGCTCCATCAAGATGAAAAGCTCTTTTTAAAACCCAAAAAAAAAAAAAA

AAAAAAAA

Deduced amino acid sequence of DBF-2 from
*Physcomitrella patens* (SEQ ID NO:9)
MSDDEVKEEKELDLTSPDVVTKYKCAAEVANKALQAVLADCKPGAKIVDLC

EKGDSSIRDLTALMYKNSKKKIDKGVAFPTCVSVNNTVCHFSPLASDESVL

AANDIVKIDLGCHVDGFIAVVAHTHVLSEGPVTGRAADVLAAAHTAAEVAL

RLVRPGKKNKDVTDAIQKVAAAYDCKIAEGVLSHQLKQFVIDANKVILSVS

NPETRVDDAEFEENEVYAIDIVTSTGDGKPKLLDEKQTTVYKRAVDKNYHL

KMKASRFIFSEINTKFPIMPFTARALEEKRARLGIVECVNHELLQPYPVLH

EKPGDCVAHIKFTVLLMPNGSDKITGLPLQECQSTKVPEDPEIKAWLALGT

KSKKKGGGKKKKGKKGDAMIEDSSETAAESATGTTDTMDTSA*

Nucleotide sequence of the partial DBF-3 from
*Physcomitrella patens* (SEQ ID NO:10)
CGGCACCAGAAAATGGTTGCCGAGAGTGTGTTGGTGTGTAGGAGCAGTGTC

GTCGGGGCTGGATTGCAGAGCTTTGTTGGAGAGGGCGCGAAGAGAGAGTCA

GCAGGGCCAGGGAGAAGCGTGTTTTTGGGAGCTCAGGTGCAGAAGATGGGA

GCGGGTATGTCCGCGCGGTCGGATGTGCGACCTGCAGCAGTTCCGAAAGCT

TCAGGAGATGTCAGTGAGCAGACTGACTATAAAACATTCAGTGATGAGGAA

TGGAAGAAGCGTCTGTCTCAACAGCAATTCTACGTCGCACGCAAGAAAGGC

ACCGAAAGACCTTTCACTGGAGAGTACTGGAACACCAAAACAGCAGGAACA

TACCTATGCGTTTGTTGTAAGACACCATTGTTCAGCTCAAAGACCAAGTTC

GACAGTGGTACCGGATGGCCATCTTACTATGACACCATAGGTGACAATGTG

AAGTCACACATGGATTGGTCGATACCCTTCATGCCCCGCACTGAGGTTGTG

TGTGCTGTGTGCGATGCTCATCTGGGTCATGTCTTCGACGATGGGCCGAGG

CCTACTGGCAAACGTTATTGTATCAACAGCGCGGCGATTGATTTGAAGGCC

GAAAGCAGAAGAGAGGGACTAGTACGTCAGGGTTTGGAAAGGGGGAATGGA

AATCAAT

Nucleotide sequence of the full-length DBF-3 from
*Physcomitrella patens* (SEQ ID NO:11)
ATCCCGGGAGAAAATGGTTGCCGAGAGTGTGTTGGTGTGTAGGAGCAGTGT

CGTCGGGGCTGGATTGCAGAGCTTTGTTGGAGAGGGCGCGAAGAGAGAGTC

AGCAGGGCCAGGGAGAAGCGTGTTTTTGGGAGCTCAGGTGCAGAAGATGGG

AGCGGGTATGTCCGCGCGGTCGGATGTGCGACCTGCAGCAGTTCCGAAAGC

TTCAGGAGATGTCAGTGAGCAGACTGACTATAAAACATTCAGTGATGAGGA

ATGGAAGAAGCGTCTGTCTCAACAGCAATTCTACGTCGCACGCAAGAAAGG

CACCGAAAGACCTTTCACTGGAGAGTACTGGAACACCAAAACAGCAGGAAC

ATACCTATGCGTTTGTTGTAAGACACCATTGTTCAGCTCAAAGACCAAGTT

CGACAGTGGTACCGGATGGCCATCTTACTATGACACCATAGGTGACAATGT

GAAGTCACACATGGATTGGTCGATACCCTTCATGCCCCGCACTGAGGTTGT

GTGTGCTGTGTGCGATGCTCATCTGGGTCATGTCTTCGACGATGGGCCGAG

GCCTACTGGCAAACGTTATTGTATCAACAGCGCGGCGATTGATTTGAAGGC

CGAGAAGCAAGAAGAGAGGAACTAGGTAGATATCAG

Deduced amino acid sequence of DBF-3 from
*Physcomitrella patens* (SEQ ID NO:12)
MVAESVLVCRSSVVGAGLQSFVGEGAKRESAGPGRSVFLGAQVQKMGAGMS

ARSDVRPAAVPKASGDVSEQTDYKTFSDEEWKKRLSQQQFYVARKKGTERP

FTGEYWNTKTAGTYLCVCCKTPLFSSKTKFDSGTGWPSYYDTIGDNVKSHM

DWSIPFMPRTEVVCAVCDAHLGHVFDDGPRPTGKRYCINSAAIDLKAEKQE

ERN*

APPENDIX-continued

Nucleotide sequence of BnDBF-1 from *Brassica napus* (SEQ ID NO:13)
CGAAGAACGAAAGAGATAAAAGAGCAACAATGGCGTTGAACGTCATCTCAT

CATCATCTTCAGCCACTTCCATTTCCATGACCTTTGCTTCCACCATCAGAG

CCTTCGTTAGACCTTCTCTCTCCCTCAGAACCACTCCATTTGCTCGCTCTC

CGTCGAAGCTTAACCTCCTTCCTCTCCCCGCCTCTCCTTCATCATTTCCTC

CGCTCCGTCTTCGTAGCCGAGGCTTCCACGGTGGTCGTGTCACAGCAATGT

CTTCTCCTGCTCCCGGATCGGTGAATAAGCCAGAGGAAGAATGGCGTGCGA

TTCTGTCTCCTGAGCAATTCAGGATCCTGAGGCAGAAAGGCACCGAATATC

CAGGAACAGGAGAATACAACAAACTATTCGAAGACGGCATCTATTCATGTG

CAGGATGTGGGACTCCTCTTTACAAATCCGCCACCAAATTCGACTCCGGTT

GTGGCTGGCCAGCTTTCTTTGACGGCCTTCCCGGTGCTATAAACCGAACTC

CTGATCCAGATGGGAGAAGAATCGAGATCACTTGTGCGGCTTGTGGGGAC

ATCTCGGCCATGTTTTCAAAGGAGAAGGTTTCCCTACACCTACCGATGAGC

GACACTGTGTGAACAGTGTTTCTCTCAAGTTCGCACCAGGGAATCAAGACT

TGTAATAATGTTCTTGGTGTTGTGTAATGCTTCTGTCTATGTCTTGTGTGT

CCTGCTCGTTATAACCAGTGTTTAGTTCCATTAATGTCGTTGAATCAAAAA

AAAAAAAAAAAAAAAAAAAAAAAAAAAAAAAAAAAAAAAAAAAAAAAAAA

AAAAAA

Deduced amino acid sequence of BnDBF-1 from *Brassica napus* (SEQ ID NO:14)
MALNVISSSSSATSISMTFASTIRAFVRPSLSLRTTPFARSPSKLNLLPLP

ASPSSFPPLRLRSRGFHGGRVTAMSSPAPGSVNKPEEEWRAILSPEQFRIL

RQKGTEYPGTGEYNKLFEDGIYSCAGCGTPLYKSATKFDSGCGWPAFFDGL

PGAINRTPDPDGRRIEITCAACGGHLGHVFKGEGFPTPTDERHCVNSVSLK

FAPGNQDL*

Nucleotide sequence of OsDBF-1 from *Oryza sativa* (SEQ ID NO:15)
CCGAAGAAAATGGCCATGCGGCAATACGCGGCTGCTACCGCTGCCTCCTCC

AGTTTCAGAGCACGTCCACGGGCGCGCCCCTCCTGCCTCCCAGCCGCCGCC

CTGCCCTTGGCGCCTTGCTGTGGTGTGGCGTGGAGCCGTGCTAGCTACAGG

CGAGCCTCCGTTCGTGCCATGGGTGCCGCTTCATCGTCTTCGTCGTCGTCG

TCGTCGTCTCCGTCGCCGCAGGGTCAAGCCCAAGCCCAAGCCCAAGGTAAA

CCGAACTACAGTACATCTCTGACTGATGAGGAGTGGAGGAAGCGCCTGACA

AAAGATCAGTATTACATTACTCGGCAGAAGGGCACAGAAAGAGCATTTACT

GGGGAATACTGGAACACCAAAACCCCGGGCATCTACCATTGTGTCTGCTGT

GACACCCCTCTTTTTGAGTCATCGACCAAATTTGATAGTGGTACTGGGTGG

CCGTCATATTATCAACCCATTGGAGATAATGTAAAGTGCAAGCTTGATATG

TCCATCATATTCATGCCTCGGACTGAGGTGCTGTGTGCTGTCTGTGACGCT

CATCTGGGGCACGTGTTTGATGATGGGCCACGACCAACAGGGAAAAGATAC

TGTATCAATAGCGCATCTCTCAAGCTGAAGAAGACCCAGTAGACCTGTGAA

GATTATGGTTACCATGTACCTACACGGCTACACTATCCGACTAGTTATAAG

GGATAGATTATGTATATAGAATATGTAAAGAATTAAGACTTGGGTATTATG

TTTACTTGTGTATCAAGAAAAAAAAAAAAAAAAAAAAAAAAAAAAAAAAA

Deduced amino acid sequence of OsDBF-1 from *Oryza sativa* (SEQ ID NO:16)
MAMRQYAAATAASSSFRARPRARPSCLPAAALPLAPCCGVAWSRASYRRAS

VRAMGAASSSSSSSSSPSPQGQAQAQAQGKPNYSTSLTDEEWRKRLTKDQ

YYITRQKGTERAFTGEYWNTKTPGIYHCVCCDTPLFESSTKFDSGTGWPSY

YQPIGDNVKCKLDMSIIFMPRTEVLCAVCDAHLGHVFDDGPRPTGKRYCIN

SASLKLKKTQ*

Nucleotide sequence of OsDBF-2 from *Oryza sativa* (SEQ ID NO:17)
GTGACCCGTGATTCGTGAACACAAACACCATCGCCATGGGCTTCAATATTC

TGAGAACCACTTCCATCTCCACTCCTATCTCTTCCTCCAAATCCAAACCCA

TTTTCTCAACTCTTCTTCGTTCTTCTCCTTCCACCATTTTCCCCCCAAAGT

CCGTTACTCCCACCACTCTTTTCGTTTCTGCCACCCCCTTCTTCACTCTCC

ATCCCAAGCTTGGTTTTCGTGGTGGGATTGTGGCCATGGCCGCACCTGGCT

CTCTCCGCAAATCCGAGGAAGAGTGGCGCGCAATTCTCTCCCCTGAACAGT

TTCGGATCCTCAGGCAAAAGGGCACCGAGTTCCCTGGAACAGGAGAGTATG

ACAAGTTCTATGAAGAGGGAGTTTACAACTGTGCTGGTTGTGGGACTCCAC

TCTACAGGTCCATAACAAAATTCAATTCTGGTTGTGGCTGGCCAGCCTTCT

ATGAGGGGATTCCCGGAGCCATAAATCGCAATCCGGATCCTGATGGGATGA

GGACAGAAATAACGTGTGCTGCTTGTGGGGGACATCTAGGTCACGTCTTTA

AAGGAGAAGGATTTCCAACACCCACTAACGAACGCCATTGTGTCAATAGCA

TTTCGCTGAAATTTGCGCCAGCCAATTCTTATTCTTAATAAAATTGAGTCT

GCTGTTTGGACGTGACTACTTAAGTACCCAACATCGGTAAAAAAATTATGC

AATGTACTTATATTATGAATGAAGTTAAAAAAAAAATGATGGAGAGAGAGA

GACCGACACGCAGCGGCCGC

Deduced amino acid sequence of OsDBF-2 from *Oryza sativa* (SEQ ID NO:18)

APPENDIX-continued

MGFNILRTTSISTPISSSKSKPIFSTLLRSSPSTIFPPKSVTPTTLFVSAT

PFFTLHPKLGFRGGIVAMAAPGSLRKSEEEWRAILSPEQFRILRQKGTEFP

APPENDIX-continued

GTGEYDKFYEEGVYNCAGCGTPLYRSITKFNSGCGWPAFYEGIPGAINRNP

DPDGMRTEITCAACGGHLGHVFKGEGFPTPTNERHCVNSISLKFAPAN

SYS*

We claim:

1. An isolated polynucleotide selected from the group consisting of:
   a) a polynucleotide having a sequence as set forth in SEQ ID NO:11; and
   b) a polynucleotide encoding a polypeptide having a sequence as set forth in SEQ ID NO:12.

2. The isolated polynucleotide of claim 1, having the sequence as set forth in SEQ ID NO:11.

3. The isolated polynucleotide of claim 1, encoding the polypeptide having the sequence as set forth in SEQ ID NO:12.

4. A vector comprising an isolated polynucleotide selected from the group consisting of:
   a) a polynucleotide having a sequence as set forth in SEQ ID NO:11; and
   b) a polynucleotide encoding a polypeptide having a sequence as set forth in SEQ ID NO:12.

5. A transgenic plant cell transformed with a polynucleotide selected from the group consisting of:
   a) a polynucleotide having a sequence as set forth in SEQ ID NO:11; and
   b) a polynucleotide encoding a polypeptide having a sequence as set forth in SEQ ID NO:12.

6. A transgenic plant transformed with a polynucleotide selected from the group consisting of:
   a) a polynucleotide having a sequence as set forth in SEQ ID NO:11; and
   b) a polynucleotide encoding a polypeptide having a sequence as set forth in SEQ ID NO:12.

7. The plant of claim 6, wherein the plant is a monocot.

8. The plant of claim 6, wherein the plant is a dicot.

9. The plant of claim 6, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and a forage crop plant.

10. A plant seed comprising a transgene selected from the group consisting of:
    a) a polynucleotide having a sequence as set forth in SEQ ID NO:11; and
    b) a polynucleotide encoding a polypeptide having a sequence as set forth in SEQ ID NO:12,
    and wherein the seed is true breeding for increased tolerance to drought.

11. The vector of claim 4, wherein the polynucleotide has the sequence as set forth in SEQ ID NO:11.

12. The vector of claim 4, wherein the polynucleotide encodes the polypeptide having the sequence as set forth in SEQ ID NO:12.

13. The transgenic plant cell of claim 5, wherein the polynucleotide has the sequence as set forth in SEQ ID NO:11.

14. The trausgenic plant cell of claim 5, wherein the polynucleotide encodes the polypeptide having the sequence as set forth in SEQ ID NO:12.

15. The plant of claim 9, wherein the plant is corn.

16. The plant of claim 9, wherein the plant is soybean.

17. The plant of claim 9, wherein the plant is canola or rapeseed.

18. The plant of claim 9, wherein the plant is cotton.

* * * * *